(12) United States Patent
Biju et al.

(10) Patent No.: US 9,783,496 B2
(45) Date of Patent: Oct. 10, 2017

(54) OXINDOLE COMPOUNDS, SOLVENT-FREE SYNTHESIS AND USE THEREOF

(71) Applicant: Council of Scientific & Industrial Research, New Delhi (IN)

(72) Inventors: Akkattu Thankappan Biju, Pune (IN); Trinadh Kaicharla, Pune (IN); Santhivardhana Reddy Yetra, Pune (IN); Tony Roy, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/781,901

(22) PCT Filed: Apr. 2, 2014

(86) PCT No.: PCT/IN2014/000208
§ 371 (c)(1),
(2) Date: Oct. 1, 2015

(87) PCT Pub. No.: WO2014/162319
PCT Pub. Date: Oct. 9, 2014

(65) Prior Publication Data
US 2016/0039755 A1 Feb. 11, 2016

(30) Foreign Application Priority Data
Apr. 2, 2013 (IN) .......................... 0992/DEL/2013

(51) Int. Cl.
| | | |
|---|---|---|
| *C07D 209/42* | (2006.01) |
| *C07D 405/12* | (2006.01) |
| *C07D 401/12* | (2006.01) |
| *C07D 409/12* | (2006.01) |
| *C07D 403/12* | (2006.01) |

(52) U.S. Cl.
CPC ......... *C07D 209/42* (2013.01); *C07D 401/12* (2013.01); *C07D 403/12* (2013.01); *C07D 405/12* (2013.01); *C07D 409/12* (2013.01)

(58) Field of Classification Search
CPC .. C07D 209/42; C07D 401/12; C07D 405/12; C07D 403/12; C07D 409/12
USPC ....................................... 546/277.7
See application file for complete search history.

(56) References Cited

U.S. PATENT DOCUMENTS 4,544,662 A * 10/1985 Brittain ................ C07D 209/38
514/374

OTHER PUBLICATIONS

Bousquet et al., "Fast and Efficient Solvent-Free Passerini Reaction," *Tetrahedron Lett.* (2012), 53:306-308, Elsevier Ltd.
Esmaeili et al., "A Novel and Efficient Synthesis of 3,3-Disubstituted Indol-2-Ones via Passerini Three-Component Reactions in the Presence of 4 Å Molecular Sieves," *Tetrahedron Lett.* (2013), 54:406-408, Elsevier, Ltd.
Kaicharla et al., "Engaging Isatins in Solvent-Free, Sterically Congested Passerini Reaction," *Green Chem.* (2013), 15:1608-1614, The Royal Society of Chemistry.
Vintonyak et al., "Identification of Thiazolidinones Spiro-Fused to Indolin-2-Ones as Potent and Selective Inhibitors of the *Mycobacterium tuberculosis* Protein Tyrosine Phosphatase B**," *Angew. Chem. Int. Ed.* (2010), 49:5902-5905, Wiley-VCH Verlag GmbH & Co., Weinheim, Germany.

* cited by examiner

*Primary Examiner* — Noble Jarrell
*Assistant Examiner* — Daniel Carcanague
(74) *Attorney, Agent, or Firm* — DLA Piper LLP (US)

(57) ABSTRACT

The present invention discloses oxindole compounds and a single step, one pot reaction for the synthesis of oxindole derivates via a solvent free Passerini reaction of isocyanides, isatins and carboxylic acids.

12 Claims, No Drawings

OXINDOLE COMPOUNDS, SOLVENT-FREE SYNTHESIS AND USE THEREOF

CROSS-REFERENCE TO RELATED APLICATIONS

This application is a 35 U.S.C §371 National Stage application of International Application No. PCT/IN2014/000208 filed Apr. 2, 2014, now pending; which claims the benefit under 35 U.S.C. §119(a) to India Application Serial No. 0992/DEL/2013 filed Apr. 2, 2013. The disclosure of each of the prior applications is considered part of and is incorporated by reference in the disclosure of this application.

FIELD OF THE INVENTION

The present invention relates to the oxindole compounds of formula A. The present invention relates to the use of oxindole compounds of formula A having antimicrobial activity. The present invention also relates to an efficient, atom-economic and environmentally-benign sterically congested Passerini reaction by employing isatins as carbonyl compound component under solvent-free conditions.

The present invention further relates to a one step, one pot reaction for the synthesis of biologically important 3-acyloxy 3-carbamoyl indol-2-ones in high yields.

BACKGROUND OF THE INVENTION

The Passerini reaction, the three-component reaction between a carboxylic acid, a carbonyl compound such as an aldehyde or a ketone, and an isocyanide, offers direct access to α-acyloxy carboxamide derivatives (Scheme 1, eq 1). This is the first isocyanide based multicomponent reaction playing a central role in combinatorial chemistry, and is widely utilized for the synthesis of various drug-like molecules, and in the total synthesis of biologically active natural products. Intriguingly, the Passerini reaction employing ketones is generally slower and in some cases, the reactions carried out with bulky carbonyl substrate and the bulky isocyanide fail to afford the desired product. However, the use of high pressure is one way to increase the efficiency of Passerini reactions involving bulky reactants.

Scheme 1: The Passerini Reaction

Classical Passerini Reaction (1921)

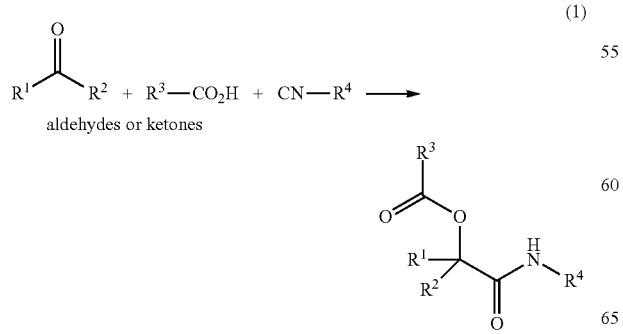

Employing Isatins in Passerini Reaction

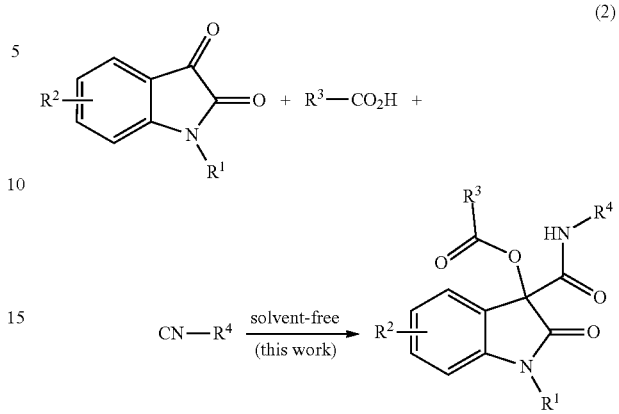

In the context of the Passerini reactions of sterically congested carbonyl compounds, it was envisaged that the multicomponent reaction involving isatin derivatives, isocyanides and carboxylic acids could provide a simple and straightforward access to oxindole derivatives (eq 2). This will be interesting because oxindoles having a quaternary benzylic centre represent a common structural motif in many natural products and biologically active compounds. Among them, the oxindoles with heteroatom at the benzylic position are useful class of compounds including the bioactive natural products (R)-convolutamydine A, maremycin B and the potent growth hormone secretion promoter SM-130686 (FIG. 1).

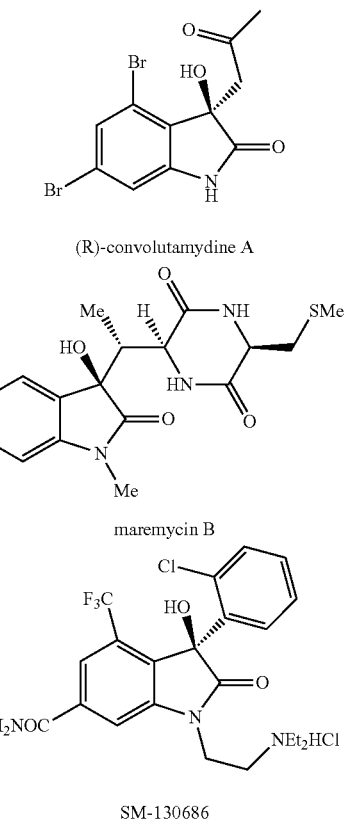

FIG. 1: Selected biologically active oxindoles having a quaternary benzylic centre having OH group.

Esmaeili et al. in "A novel and efficient synthesis of 3,3-disubstituted indol-2-ones via Passerini three-component reactions in the presence of 4 Å molecular sieves" in Tetrahedron Letters 54 (2013) 406-408 report the Passerini coupling of cyclohexyl isocyanide with isatins and carboxylic acids in the presence of 4 Å molecular sieves. This process offers a highly efficient and atom-economic access to 3-acyloxy-3-carboxamido-1,3-dihydro-2H-indol-2-ones in high to excellent yields, but the reaction proceeds only in the presence of a solvent. Moreover, this reaction is limited only to cyclohexyl isocyanide, and the scope of the reaction is not broad. An article titled "Fast and efficient solvent-free Passerini reaction" by Till Bousquet et a. in Tetrahedron Letters 01/2012; 53(3):306-308 reports Passerini three component condensation between a carboxylic acid, an aldehyde, and an isocyanide at high temperature under solvent-free conditions was developed. This methodology allows the formation of a broad range of α-acyloxyamides in excellent yields in short reaction times, but suffers from drawbacks including being restricted to aldehydes and being conducted at higher temperatures.

Hence, an easier, efficient and environment friendly process for the synthesis of oxindole derivatives is highly desired to overcome the above mentioned problems. Further, it would be desirable to improve yields over prior art processes and also to conduct the process at milder conditions including low temperatures.

OBJECTS OF THE INVENTION

The main object of the present invention is to provide a facile, atom-economic and environmentally-benign protocol for the synthesis of biologically important oxindole derivatives in high yields.

Another object of the present invention is to provide a process for the synthesis of biologically important oxindole derivatives in high yields by employing isatins as carbonyl compound surrogates in Passerini reaction carried out under solvent-free conditions.

SUMMARY OF THE INVENTION

The present invention provides a practical and efficient solvent-free. Passerini reaction of isocyanides, isatins and carboxylic acids, leading to the formation of 3,3-disubstituted oxindole derivatives, wherein the reaction is carried out in the presence of air.

The present invention also provides the use of electrophilic phenols as the acid component in the above mentioned reactions and establishes the utility of the reaction by a one-pot synthesis of oxindoles with free —OH group at the benzylic position.

Accordingly the present invention provides oxindole compounds of formula A,

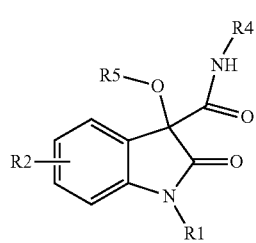

Formula A wherein, $R^1$=Alkyl, H, Allyl, or Phenyl; $R^2$=H, Br, Cl, F, or $NO_2$; $R^3$=(hetero) aryl, or alkyl; $R^4$=t-Bu, Cyclohexyl, i-Pr, or $CH_2$—$CO_2Et$; and

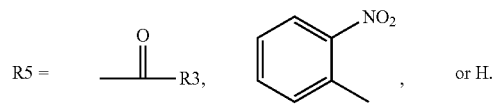

In an embodiment of the present invention, the oxindole compound of formula A is selected from the group consisting of:

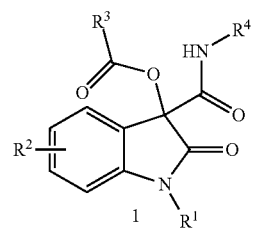

Formula 4 wherein, $R^1$=Alkyl, H, Allyl, or Phenyl;
$R^2$=H, Br, Cl, F, or $NO_2$;
$R^3$=(hetero) aryl, or alkyl; and
$R^4$=t-Bu, Cy, i-Pr, or $CH_2$—$CO_2Et$
and, formula 6

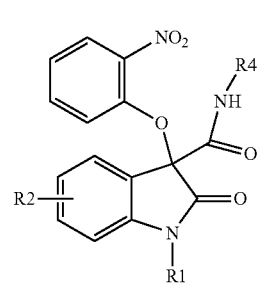

Formula 6 wherein, $R^1$=Alkyl, H, Allyl, or Phenyl;
$R^2$=H, Br, Cl, F, or $NO_2$;
$R^3$=(hetero) aryl, or alkyl; and
$R^4$=t-Bu, Cy, i-Pr, or $CH_2$—$CO_2Et$.

In still another embodiment of the present invention, the oxindole compound of formula A selected from the group consisting of:
i. 3-(tert-Butylcarbamoyl)-1-methyl-2-oxoindolin-3-yl benzoate (4a);
ii. 3-(tert-Butylcarbamoyl)-1-methyl-2-oxoindolin-3-yl 2-fluoro benzoate (4b);
iii. 3-(tert-Butylcarbamoyl)-1-methyl-2-oxoindolin-3-yl 2-chloro benzoate (4c);
iv. 3-(tert-butylcarbamoyl)-1-methyl-2-oxoindolin-3-yl 2-bromo benzoate (4d);
v. 3-(tert-Butylcarbamoyl)-1-methyl-2-oxoindolin-3-yl 3-nitro benzoate (4e);
vi. 3-(tert-Butylcarbamoyl)-1-methyl-2-oxoindolin-3-yl 4-nitro benzoate (4f);
vii. 3-(tert-Butylcarbamoyl)-1-methyl-2-oxoindolin-3-yl 4-methoxy benzoate (4g);

viii. 3-(tert-Butylcarbamoyl)-1-methyl-2-oxoindolin-3-yl furan-2-carboxylate (4h);
ix. 3-(tert-Butylcarbamoyl)-1-methyl-2-oxoindolin-3-yl thiophene-2-carboxylate (4i);
x. 3-(tert-Butylcarbamoyl)-1-methyl-2-oxoindolin-3-yl benzofuran-2-carboxylate (4j);
xi. 3-(tert-Butylcarbamoyl)-1-methyl-2-oxoindolin-3-yl 1H-indole-2-carboxylate (4k);
xii. 3-(tert-Butylcarbamoyl)-1-methyl-2-oxoindolin-3-yl picolinate (4l);
xiii. 3-(tert-Butylcarbamoyl)-1-methyl-2-oxoindolin-3-yl cinnamate (4m);
xiv. 3-(tert-Butylcarbamoyl)-1-methyl-2-oxoindolin-3-yl acetate (4n);
xv. 3-(tert-Butylcarbamoyl)-1-methyl-2-oxoindolin-3-yl propionate (4o);
xvi. 3-(tert-Butylcarbamoyl)-1-methyl-2-oxoindolin-3-yl 2-(4-methoxyphenyl)acetate (4p);
xvii. 1-Benzyl-3-(tert-Butylcarbamoyl)-2-oxoindolin-3-yl benzoate (4q);
xviii. 1-Allyl-3-(tert-Butylcarbamoyl)-2-oxoindolin-3-yl benzoate (4r);
xix. 3-(tert-Butylcarbamoyl)-2-oxoindolin-3-yl benzoate (4s);
xx. 3-(tert-Butylcarbamoyl)-1-methyl-5-nitro-2-oxoindolin-3-yl benzoate (4t);
xxi. 3-(tert-Butylcarbamoyl)-5-fluoro-1-methyl-2-oxoindolin-3-yl benzoate (4u);
xxii. 3-(tert-Butylcarbamoyl)-5-chloro-1-methyl-2-oxoindolin-3-yl benzoate (4v);
xxiii. 5-Bromo-3-(tert-Butylcarbamoyl)-1-methyl-2-oxoindolin-3-yl benzoate (4w);
xxiv. 3-(Cyclohexylcarbamoyl)-1-methyl-2-oxoindolin-3-yl benzoate (4x);
xxv. 3-(Isopropylcarbamoyl)-1-methyl-2-oxoindolin-3-yl benzoate (4y);
xxvi. 3-((2-Ethoxy-2-oxoethyl)carbamoyl)-1-methyl-2-oxoindolin-3-yl benzoate (4z);
xxvii. N-(tert-Butyl)-1-methyl-3-(2-nitrophenoxy)-2-oxoindoline-3-carboxamide (6a);
xxviii. 5-Bromo-N-(tert-butyl)-1-methyl-3-(2-nitrophenoxy)-2-oxoindoline-3-carboxamide (6b);
xxix. N-Cyclohexyl-1-methyl-3-(2-nitrophenoxy)-2-oxoindoline-3-carboxamide (6c); and
xxx. 5-Bromo-N-(tert-Butyl)-3-hydroxy-1-methyl-2-oxoindoline-3-carboxamide (7).

In yet another embodiment of the present invention, the oxindole compound of formula A is useful as anti tubercular agent.

In another embodiment of the present invention there is provided a single step, one pot process for the synthesis of oxindole compounds of general formula A, comprising the steps of:
  (a) reacting carboxylic acid 2 or electron-deficient phenol 5 with an isatin derivative 1 and an isocyanide 3 in the presence of air to obtain a reaction mixture;
  (b) heating the reaction mixture as obtained in step (a) under solvent-free conditions to obtain a crude reaction mixture;
  (c) purifying the crude reaction mixture obtained in step (b) by column chromatography to obtain the oxindole compounds of formula A consisting of formula 4 and formula 6; and
  (d) hydrolyzing the crude reaction mixture obtained in step (b) to obtain compound of formula A consisting of formula 7.

In still another embodiment of the present invention, the heating in step (b) is carried out in a preheated oil bath at a temperature from 60 to 100° C. for a period of 8-12 h.

In yet another embodiment of the present invention, the carboxylic acid used in the synthesis of oxindole compounds of general formula A, is selected from the group consisting of substituted and unsubstituted benzoic acid, heterocyclic carboxylic acids, N-unprotected indole 2-carboxylic acid, α,β-unsaturated acid, and aliphatic acids. In another embodiment of the present invention, the carboxylic acid is acetic acid.

In still another embodiment of the present invention, the isatin derivative 1 is selected from the group consisting of unprotected isatin, substituted isatin derivatives having substituent on nitrogen of isatin and substituted isatin derivative having substituents at the carbocyclic ring of isatin.

In yet another embodiment of the present invention, the substituent on nitrogen of isatin is selected from benzyl group or allyl moiety.

In yet another embodiment of the present invention, the isocyanide used in the synthesis of oxindole compounds of general formula A, having substituent on nitrogen of isocyanide is selected from the group consisting of t-Bu, Cy, i-Pr, and CH2-CO2Et.

In still another embodiment of the present invention, the yield of oxindole compounds of formula A under solvent-free conditions in the presence of air is in the range of 80% to 96%.

In yet another embodiment of the present invention, the electron-deficient phenol used for the synthesis of O-arylated oxindole derivative (formula 6) is 2-nitro phenol.

In still another embodiment of the present invention, the yield of O-arylated oxindole derivatives 6 is 40% to 55%.

DETAILED DESCRIPTION OF THE INVENTION

In view of the above, the present invention provides a facile, atom-economic and environmentally-benign protocol for the synthesis of biologically important oxindole derivatives in high yields by employing isatins as carbonyl compound surrogates in Passerini reaction carried out under solvent-free conditions.

In an embodiment, present invention provides oxindole compounds of formula A,

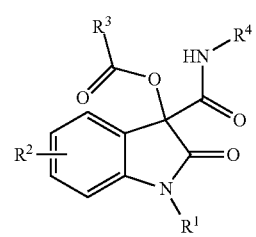

Formula A

Wherein, $R^1$=Alkyl; $R^2$=Br, Cl, F, or $NO_2$; $R^3$=(hetero)aryl, or alkyl; $R^4$=t-Bu, Cy, or i-Pr.

Another embodiment of the present invention provides a single step, one pot reaction for the synthesis of oxindole derivates of general formula A via a solvent free Passerini reaction of isocyanides, isatins and carboxylic acids, carried out in the presence of air.

Still another embodiment of the present invention provides a process for the synthesis of oxindole derivatives of general formula A comprising the steps of:
(a) reacting carboxylic acid 2 or electron-deficient phenol 5 with an isatin derivative 1 and an isocyanide 3 in the presence of air to obtain a reaction mixture;
(b) heating the reaction mixture obtained step (a) under solvent-free conditions to obtain a crude reaction mixture;
(c) purifying the crude reaction mixture obtained in step (b) by column chromatography to obtain the desired products.

The process is shown below in Scheme: A

Scheme: A

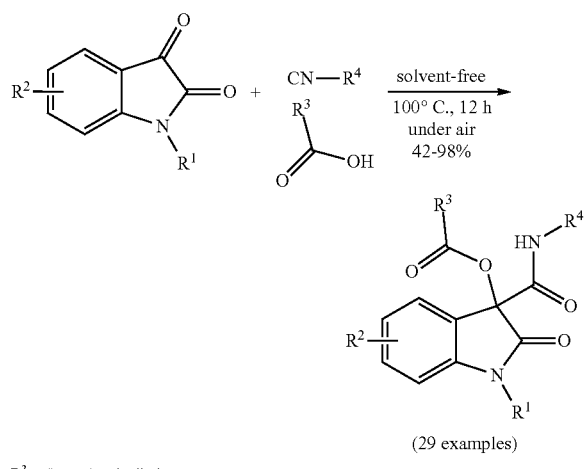

(29 examples)

$R^3$ = (hetero)aryl, alkyl

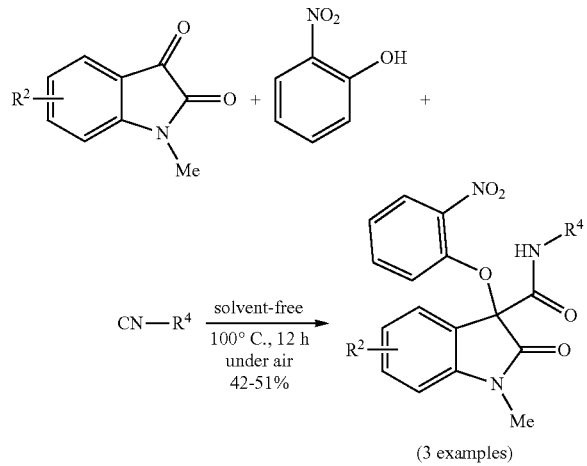

(3 examples)

wherein, $R^1$=Alkyl; $R^2$=Br, Cl, F, or $NO_2$; $R^3$=(hetero)aryl, or alkyl; $R^4$=t-Bu, Cyclohexyl, i-Pr, or CH2-CO2-Et.

In another embodiment of the present invention provides a process for the synthesis of oxindole compounds of formula A with >95% yields.

In an embodiment the present invention provides the process wherein the solvent can be selected from the group consisting of $CH_2Cl_2$, $CHCl_3$, THF and $CH_3CN$ to obtain 49% to 80% yield.

In another embodiment, present invention provides a process for the synthesis of oxindole compounds under solvent-free conditions in the presence of air to obtain 80% to 96% yield.

In an embodiment the present invention provides a process wherein the substituted isatin derivatives and isocyanides (Table 3) is selected from substituents on nitrogen of isatin including benzyl group and allyl moiety (4q, 4r), unprotected isatin t (4s), various substituents at the carbocyclic ring of isatin (4t-w), and isocyanides (4x-z).

In a preferred embodiment the present invention provides a process for the synthesis of oxindole derivatives encompassing 3-(tert-Butylcarbamoyl)-1-methyl-2-oxoindolin-3-yl benzoate (4a), 3-(tert-Butylcarbamoyl)-1-methyl-2-oxoindolin-3-yl 2-fluoro benzoate (4b), 3-(tert-Butylcarbamoyl)-1-methyl-2-oxoindolin-3-yl 2-chloro benzoate (4c), 3-(tert-butylcarbamoyl)-1-methyl-2-oxoindolin-3-yl 2-bromo benzoate (4d), 3-(tert-Butylcarbamoyl)-1-methyl-2-oxoindolin-3-yl 3-nitro benzoate (4e), 3-(tert-Butylcarbamoyl)-1-methyl-2-oxoindolin-3-yl 4-nitro benzoate (4f), 3-(tert-Butylcarbamoyl)-1-methyl-2-oxoindolin-3-yl 4-methoxy benzoate (4g), 3-(tert-Butylcarbamoyl)-1-methyl-2-oxoindolin-3-yl furan-2-carboxylate (4h), 3-(tert-Butylcarbamoyl)-1-methyl-2-oxoindolin-3-yl thiophene-2-carboxylate (4i), 3-(tert-Butylcarbamoyl)-1-methyl-2-oxoindolin-3-yl benzofuran-2-carboxylate (4j), 3-(tert-Butylcarbamoyl)-1-methyl-2-oxoindolin-3-yl 1H-indole-2-carboxylate (4k), 3-(tert-Butylcarbamoyl)-1-methyl-2-oxoindolin-3-yl picolinate (4l), 3-(tert-Butylcarbamoyl)-1-methyl-2-oxoindolin-3-yl cinnamate (4m), 3-(tert-Butylcarbamoyl)-1-methyl-2-oxoindolin-3-yl acetate (4n), 3-(tert-Butylcarbamoyl)-1-methyl-2-oxoindolin-3-yl propionate (4o), 3-(tert-Butylcarbamoyl)-1-methyl-2-oxoindolin-3-yl 2-(4-methoxyphenyl)acetate (4p), 1-Benzyl-3-(tert-Butylcarbamoyl)-2-oxoindolin-3-yl benzoate (4q), 1-Allyl-3-(tert-Butylcarbamoyl)-2-oxoindolin-3-yl benzoate (4r), 3-(tert-Butylcarbamoyl)-2-oxoindolin-3-yl benzoate (4s), 3-(tert-Butylcarbamoyl)-1-methyl-5-nitro-2-oxoindolin-3-yl benzoate (4t), 3-(Bert-Butylcarbamoyl)-5-fluoro-1-methyl-2-oxoindolin-3-yl benzoate (4u), 3-(tert-Butylcarbamoyl)-5-chloro-1-methyl-2-oxoindolin-3-yl benzoate (4v), 5-Bromo-3-(tert-Butylcarbamoyl)-1-methyl-2-oxoindolin-3-yl benzoate (4w), 3-(Cyclohexylcarbamoyl)-1-methyl-2-oxoindolin-3-yl benzoate (4x), 3-(Isopropylcarbamoyl)-1-methyl-2-oxoindolin-3-yl benzoate (4y), and 3-((2-Ethoxy-2-oxoethyl)carbamoyl)-1-methyl-2-oxoindolin-3-yl benzoate (4z).

In an embodiment of the present invention provides a process for the synthesis of O-arylated oxindole derivative (formula 6) wherein the electron-deficient phenol is 2-nitro phenol, and is treated with N-substituted isatins 1 and isocyanides 3 to obtain the desired O-arylated oxindole derivatives 6 in 40% to 55% yields (Table 4).

In an embodiment of the present invention provides a process for the synthesis of oxindoles with free —OH group at the benzylic position with a base-mediated hydrolysis under mild conditions furnishing the oxindole derivative 7 in 91% yield (Scheme 2).

Scheme 2: One-Pot Synthesis of Oxindoles with Free -OH Group at the Benzylic Position

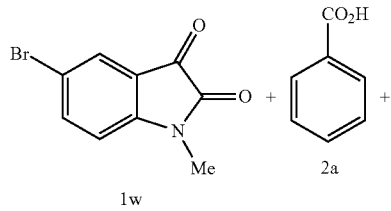

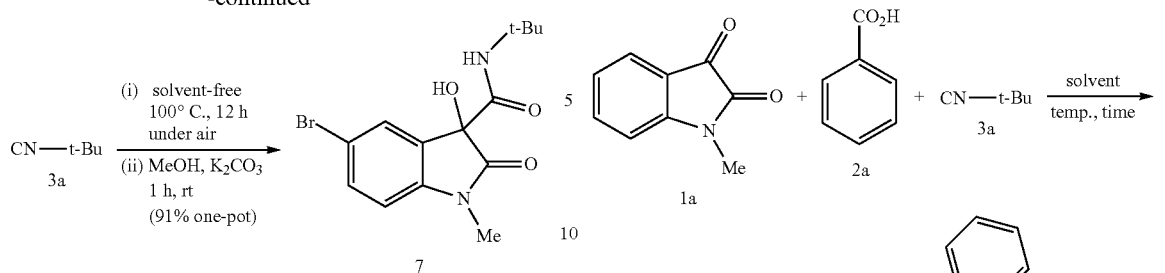

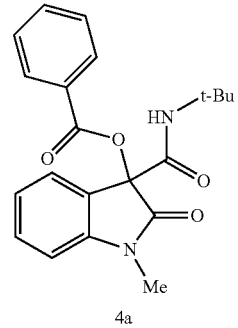

The invention will now be described in detail in connection with certain preferred and optional embodiments, so that various aspects thereof may be more fully understood and appreciated.

EXAMPLES

Experimental section: Reaction temperature is reported as the temperature of the bath surrounding the reaction vessel. $^1$H and $^{13}$C NMR spectra were recorded on Bruker AV 400, in solvents as indicated. Chemical shifts (δ) are given in ppm. The residual solvent signals were used as references and the chemical shifts converted to the TMS scale (CDCl$_3$: δH=7.26 ppm, δC=77.16 ppm). Infrared spectra were recorded on a Perkin-Elmer 1615 FT Infrared Spectrophotometer Model 60B. The wave numbers (n) of recorded IR-signals are quoted in cm$^{-1}$. HRMS data were recorded on a Thermo Scientific Q-Exactive, Accela 1250 pump. Analytical thin layer chromatography was performed on TLC Silica gel 60 F$_{254}$.

General Procedure for the Solvent-Free Passerini Reaction: To a flame-dried screw-capped test tube equipped with a magnetic stir bar was added the isatin compound 1 (0.5 mmol, 1.0 equiv) the isocyanide 3 (0.6 mmol, 1.2 equiv) and carboxylic acid 2 or 2-nitrophenol 5 (0.75 mmol, 1.5 equiv) in the presence of air. Then the reaction mixture was placed in preheated oil bath at 100° C. for 12 h under solvent-free conditions. Then the crude reaction mixture was purified by silica gel column chromatography (eluting with CH$_2$Cl$_2$-EtOAc solvent system, typically 1% EtOAc in CH$_2$Cl$_2$).

Opimization of the Reaction Condition: The treatment of N-methyl isatin 1a with benzoic acid 2a and tert-butyl isocyanide 3a in different solvents was carried out. When the reaction was carried out in CH$_2$Cl$_2$ at 25° C., the expected product 3-benzoyloxy 3-carbamoyl indol-2-one derivative 4a was formed in 49% yield (based on $^1$H NMR spectroscopy, Table 1, entry 1). Increasing the reaction temperature resulted in improved yield of the product (entry 2). Moreover, the reactions carried out in CHCl$_3$ at a higher temperature furnished higher yields of the product (entries 3,4). However, other chlorinated solvent including CH$_2$Cl$_2$ and solvents like THF and CH$_3$CN afforded the product in low yields (entries 5-7). When the reaction was carried out under solvent-free conditions at 80° C., the product 4a was formed in 82% yield (entry 8). Increasing the reaction temperature under solvent-free conditions improved the yield of 4a, and finally when the reaction was carried out at 100° C. under solvent-free conditions in air for 12 h, 4a was isolated in 91% yield (entry 10).

TABLE 1

Optimization of the Reaction Conditions[a]

| entry | 2a (equiv) | 3a (equiv) | solvent | temp. (° C.) | time (h) | yield of 4a (%)[b] |
|---|---|---|---|---|---|---|
| 1 | 1.0 | 1.0 | CH$_2$Cl$_2$ | 25 | 24 | 49 |
| 2 | 1.0 | 1.0 | CH$_2$Cl$_2$ | 50 | 24 | 57 |
| 3 | 1.0 | 1.0 | CHCl$_3$ | 70 | 24 | 61 |
| 4 | 1.5 | 1.5 | CHCl$_3$ | 80 | 24 | 76 |
| 5 | 1.0 | 1.0 | (CH$_2$Cl)$_2$ | 80 | 24 | 60 |
| 6 | 1.0 | 1.0 | THF | 70 | 24 | 33 |
| 7 | 1.0 | 1.0 | CH$_3$CN | 70 | 24 | 63 |
| 8 | 1.5 | 1.2 | solvent-free | 80 | 24 | 82 |
| 9 | 1.5 | 1.2 | solvent-free | 90 | 20 | 92 |
| 10 | 1.5 | 1.2 | solvent-free under air | 100 | 12 | 96(91)[c] |

[a]All reactions were carried out in 0.25 mmol scale of 1a in 1.0 mL solvent under Ar atmosphere unless otherwise specified.
[b]The yields were determined by $^1$H NMR analysis of crude products using CH$_2$Br$_2$ as the internal standard.
[c]Isolated yield at 0.50 mmol scale in parentheses.

Investigation on substrate scope of the reaction: Firstly, we evaluated the variation of the carboxylic acid moiety (Table 2). The unsubstituted benzoic acid and a variety of electron releasing and -withdrawing groups at various position of the aromatic ring of benzoic acid afforded the oxindole derivatives in ≥80% in all cases (4a-g). A range of heterocyclic carboxylic acids also resulted in the smooth conversion to the desired product further expanding the scope of this three-component reaction (4h-l). N-unprotected indole 2-carboxylic acid also afforded the expected product 4k in moderate yield. Moreover, the reaction of α,β-unsaturated acid furnished excellent yield of the oxindole derivative 4m. Furthermore, the reaction is not limited to aromatic and α,β-unsaturated acids, but instead aliphatic acids including acetic acid also afforded the desired products in moderate yields (4n-p).

Next, the scope of this reaction with various substituted isatin derivatives and isocyanides (Table 3) was studied. Substituents on nitrogen of isatin including benzyl group and allyl moiety, and unprotected isatin also afforded moderate yield of the Passerini adduct (4s). Moreover, various substituents at the carbocyclic ring of isatin also underwent smooth three-component reaction leading to the desired product in excellent yield (4t-w). Furthermore, various isocyanides also furnished good to excellent yields of the desired products (4x-z).

TABLE 2

Employing Isatins in Solvent-free Passerini Reaction: Scope of Carboxylic Acids

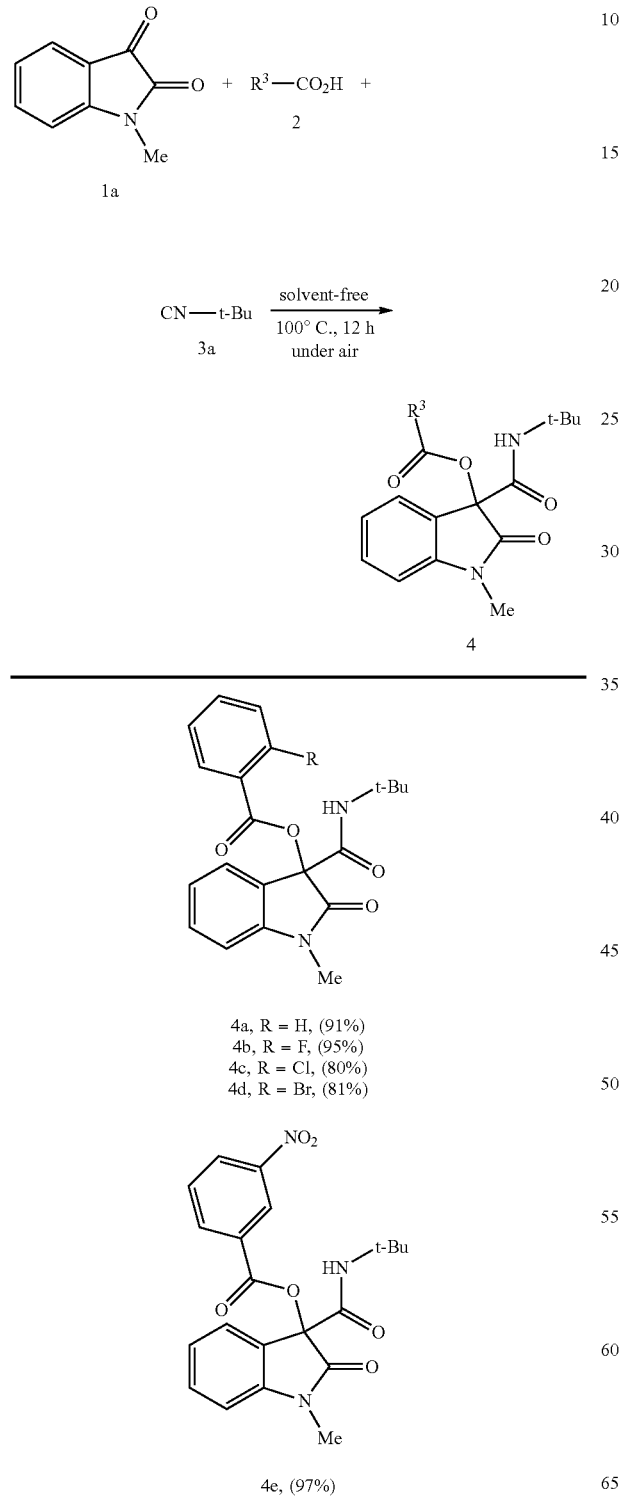

TABLE 2-continued

Employing Isatins in Solvent-free Passerini Reaction: Scope of Carboxylic Acids

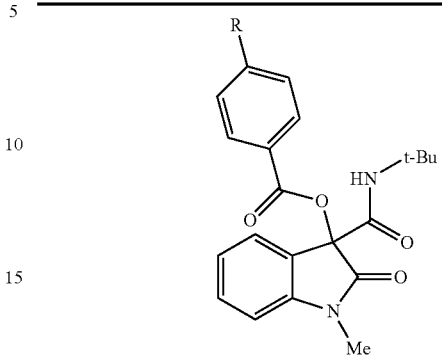

4f, R = $NO_2$, (98%)
4g, R = OMe, (97%)

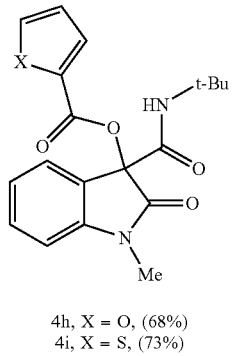

4h, X = O, (68%)
4i, X = S, (73%)

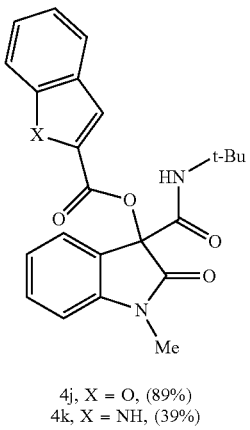

4j, X = O, (89%)
4k, X = NH, (39%)

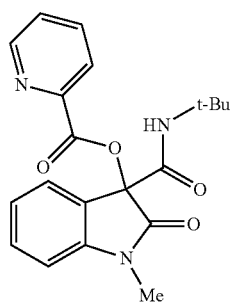 [SMILES: CN1C(=O)C(OC(=O)c2ccccn2)(C(=O)NC(C)(C)C)c2ccccc21]

4l, (65%)

TABLE 2-continued

Employing Isatins in Solvent-free Passerini Reaction: Scope of Carboxylic Acids

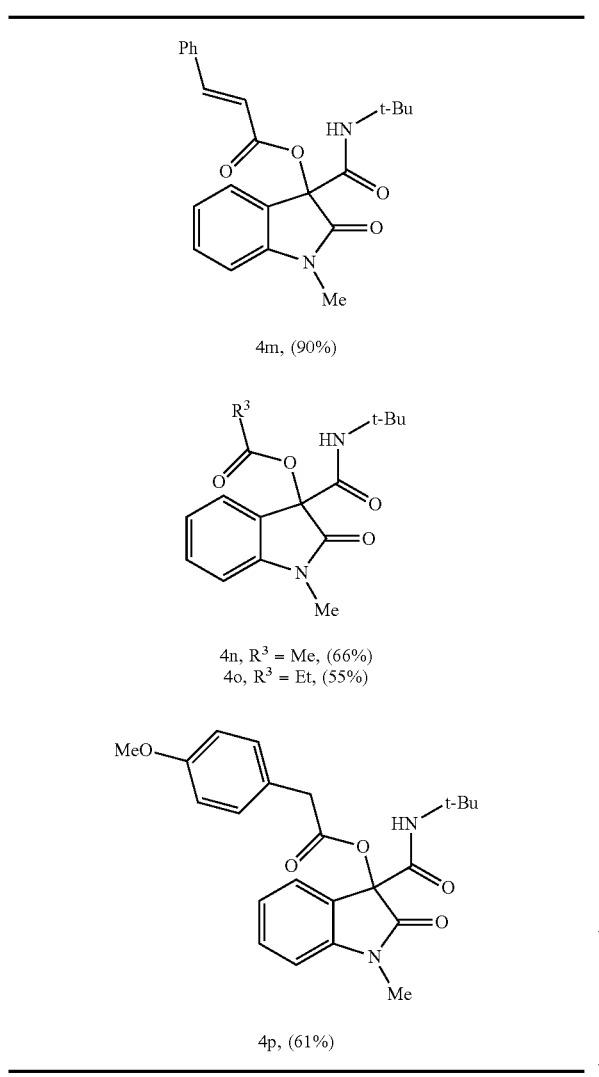

4m, (90%)

4n, R³ = Me, (66%)
4o, R³ = Et, (55%)

4p, (61%)

[a] General conditions: 1a (0.50 mmol), 2 (0.75 mmol), 3a (0.60 mmol) solvent-free conditions under air, 100° C. and 12 h.

TABLE 3

Variation of the Isatin Moiety and Isocyanide Moiety

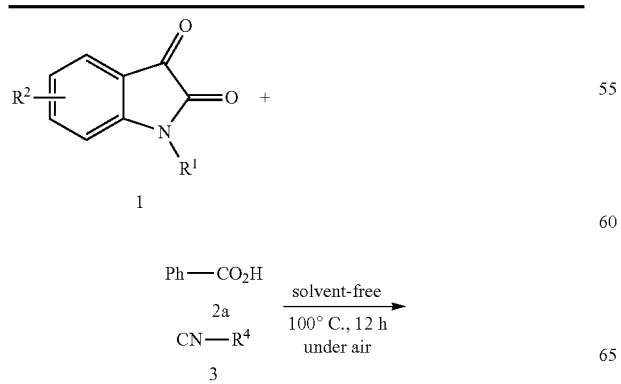

TABLE 3-continued

Variation of the Isatin Moiety and Isocyanide Moiety

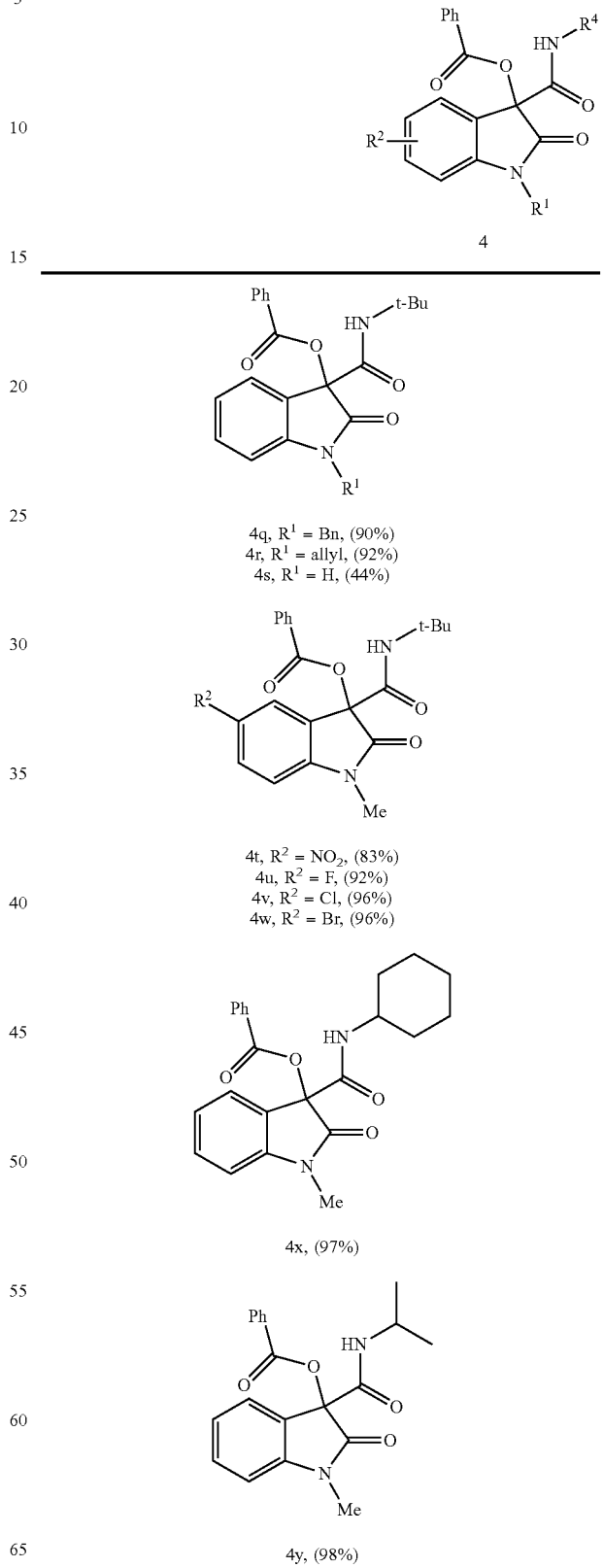

4q, R¹ = Bn, (90%)
4r, R¹ = allyl, (92%)
4s, R¹ = H, (44%)

4t, R² = NO₂, (83%)
4u, R² = F, (92%)
4v, R² = Cl, (96%)
4w, R² = Br, (96%)

4x, (97%)

4y, (98%)

TABLE 3-continued

Variation of the Isatin Moiety and Isocyanide Moiety

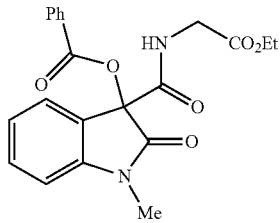 [SMILES: CCOC(=O)CNC(=O)C1(OC(=O)c2ccccc2)C(=O)N(C)c2ccccc21]

4z, (76%)

[a] General conditions: 1 (0.50 mmol), 2a (0.75 mmol), 3 (0.60 mmol) solvent-free conditions under air, 100° C. and 12 h.

Utility of 2-Nitrophenol as Acid Surrogate

The synthetic potential of this solvent-free Passerini reaction has been demonstrated by utilizing electron-deficient phenols as the acid component in the reaction. Treatment of N-substituted isatins 1 with 2-nitrophenol 5 and isocyanides 3 under the optimized reaction conditions resulted in the synthesis of O-arylated oxindole derivative 6 in moderate yields (Table 4). This reaction is an example of the use of Smiles rearrangement in Passerini reaction and the key step is the irreversible Smiles rearrangement of the intermediate phenoxyimidate adducts leading to the formation of the O-arylated product 6. The substituted isatin derivative as well as cyclohexylisocyanide worked in the O-arylative Passerini reaction under solvent-free conditions leading to moderate yield of the product (6a-c).

TABLE 4

Utility of 2-Nitrophenol in the Reaction as Acid Surrogate

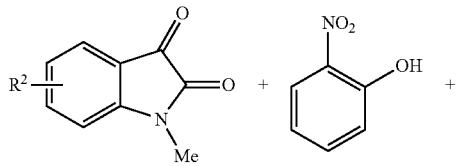

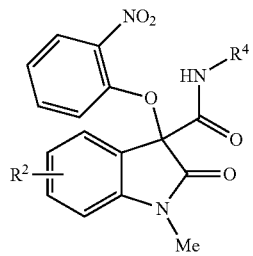

TABLE 4-continued

Utility of 2-Nitrophenol in the Reaction as Acid Surrogate

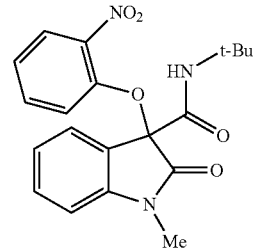 [SMILES: CN1C(=O)C(Oc2ccccc2[N+](=O)[O-])(C(=O)NC(C)(C)C)c2ccccc21]

6a, (44%)

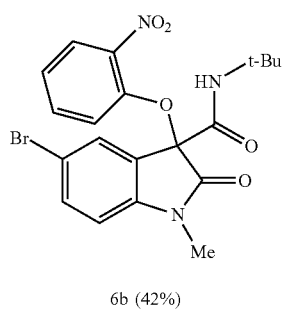

6b (42%)

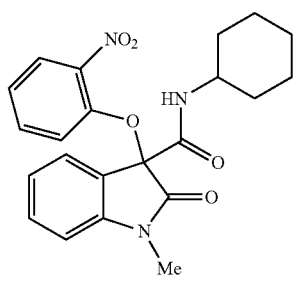 [SMILES: CN1C(=O)C(Oc2ccccc2[N+](=O)[O-])(C(=O)NC2CCCCC2)c2ccccc21]

6c (51%)

[a] General conditions: 1 (0.50 mmol), 5 (0.75 mmol), 3 (0.60 mmol) solvent-free conditions under air, 100° C. and 12 h.

One-Pot Synthesis of Oxindoles with Free —OH Group

The synthetic utility of the present methodology was further examined by the one-pot synthesis of oxindoles with free —OH group at the benzylic position by combining the Passerini reaction employing isatins with a base-mediated hydrolysis under mild conditions. The one-pot reaction afforded the oxindole derivative 7 in 91% yield (Scheme 2).

Scheme 2: One-Pot Synthesis of Oxindoles with Free -OH Group at the Benzylic Position

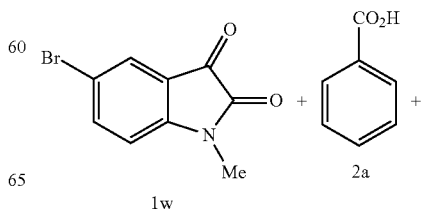

-continued

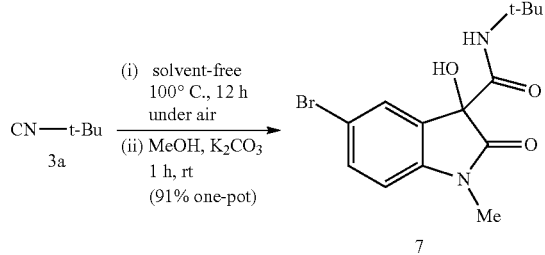

(i) solvent-free 100° C., 12 h under air
(ii) MeOH, K₂CO₃ 1 h, rt
(91% one-pot)

Example 1

3-(tert-Butylcarbamoyl)-1-methyl-2-oxoindolin-3-yl benzoate (4a)

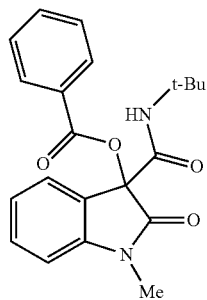 [SMILES: CN1C(=O)C(OC(=O)c2ccccc2)(C(=O)NC(C)(C)C)c2ccccc21]

$R_f$ (EtOAc/DCM=5/95): 0.55; ¹H NMR (400 MHz, CDCl₃); δ 7.99 (d, J=7.2 Hz, 2H), 7.61 (t, J=7.5 Hz, 1H), 7.46 (t, J=7.5 Hz, 2H), 7.39-7.34 (m, 2H), 7.07 (t, J=7.5 Hz, 1H), 6.92 (d, J=7.7 Hz, 1H), 6.81 (bs, 1H), 3.32 (s, 3H), 1.44 (s, 9H). ¹³C NMR (100 MHz, CDCl₃); δ 171.70, 163.73, 163.25, 145.25, 134.03, 130.82, 130.19, 129.97, 128.79, 128.58, 125.13, 124.16, 123.29, 108.92, 81.22, 52.23, 28.69, 27.04. HRMS calculated [M+H]⁺ for $C_{21}H_{23}O_4N_2$: 367.1652, found: 367.1650. FTIR (cm⁻¹): 3440, 3020, 2931, 17331, 1690, 1617, 1518, 1472, 1269, 1216, 1109, 1068, 1024, 754, 710.

Example 2

3-(tert-Butylcarbamoyl)-1-methyl-2-oxoindolin-3-yl 2-fluoro benzoate (4b)

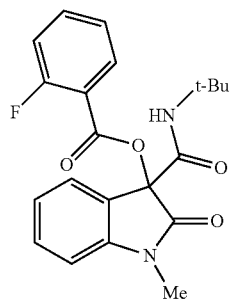 [SMILES: CN1C(=O)C(OC(=O)c2ccccc2F)(C(=O)NC(C)(C)C)c2ccccc21]

$R_f$ (EtOAc/DCM=5/95): 0.50; ¹H NMR (400 MHz, CDCl₃): δ 7.91 (t, J=7.6 Hz, 1H), 7.63-7.59 (m, 1H), 7.40 (t, J=7.8 Hz, 1H), 7.42-7.21 (m, 4H), 7.07 (t, J=7.6 Hz, 1H), 6.95 (d, J=7.6 Hz, 1H), 3.34 (s, 3H), 1.46 (s, 9H). ¹³C NMR (100 MHz, CDCl₃): δ 171.03, 163.75, 162.20 (d, J=257.2 Hz), 161.04 (d, J=3.2 Hz), 145.71, 136.09, 136.0, 133.36, 130.92, 125.61, 124.76 (d, J=3.3 Hz), 122.50 (d, J=9.67), 117.29 (d, J=23.3 Hz), 116.78 (d, J=9.7 Hz), 108.99, 81.74, 52.11, 28.64, 27.01. HRMS calculated [M+H]⁺ for $C_{21}H_{22}O_4N_2F$: 385.1558, found: 385.1556. FTIR (cm⁻¹): 3428, 3019, 1735, 1686, 1614, 1524, 1369, 1300, 1216, 1119, 755, 669.

Example 3

3-(tert-Butylcarbamoyl)-1-methyl-2-oxoindolin-3-yl 2-chloro benzoate (4c)

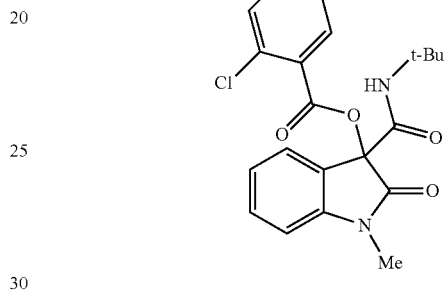

$R_f$ (EtOAc/DCM=5/95): 0.43; ¹H NMR (400 MHz, CDCl₃): δ 7.87 (d, J=7.8 Hz, 1H), 7.51-7.47 (m, 2H), 7.41-7.28 (m, 3H), 7.12-7.07 (m, 2H), 6.90 (d, J=7.8 Hz, 1H), 3.31 (s, 3H) 1.41 (s, 9H). ¹³C NMR (100 MHz, CDCl₃): δ 171.12, 163.55, 162.63, 145.66, 133.92, 133.42, 133.24, 131.41, 130.89, 128.33, 127.28, 125.40, 123.26, 109.02, 82.17, 52.30, 28.69, 27.01. HRMS calculated [M+H]⁺ for $C_{21}H_{22}O_4N_2Cl$: 401.1263, found: 401.1259. FTIR (cm⁻¹) 3671, 3440, 3352, 2970, 2936, 2253, 1719, 1691, 1607, 1581, 1494, 1471, 1352, 1260, 1169, 1106, 1030, 911, 846, 732, 648.

Example 4

3-(tert-butylcarbamoyl)-1-methyl-2-oxoindolin-3-yl 2-bromo benzoate (4d)

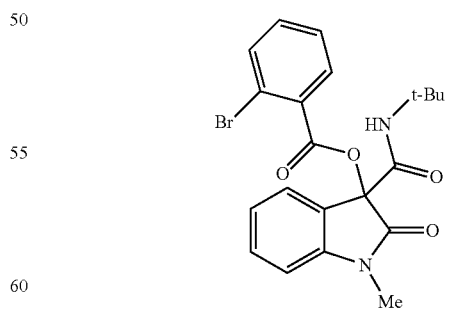

$R_f$ (EtOAc/DCM=5/95): 0.52; ¹H NMR (400 MHz, CDCl₃) δ 7.80-7.78 (m, 1H), 7.69-7.67 (m, 1H), 7.40-7.33 (m, 4H), 7.09-7.06 (m, 2H), 6.90 (d, J=7.9 Hz, 1H), 3.32 (s, 3H), 1.41 (s, 9H). ¹³C NMR (100 MHz, CDCl₃) δ 171.11, 163.47, 145.66, 145.66, 134.59, 133.79, 133.11, 130.88, 130.73, 127.79, 125.35, 123.55, 123.22, 121.30, 109.03, 82.21, 52.37, 28.75, 27.02. HRMS calculated [M+H]⁺ for $C_{21}H_{22}O_4N_2Br$: 445.0757, found: 445.0756. FTIR (cm⁻¹): 3407, 2969, 1734, 1686, 1614, 1590, 1433, 1115, 1025, 874, 748.

Example 5

3-(tert-Butylcarbamoyl)-1-methyl-2-oxoindolin-3-yl 3-nitro benzoate (4e)

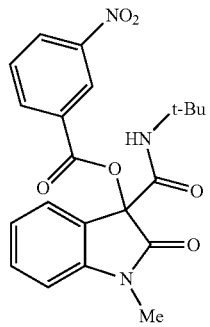 [SMILES: CN1C(=O)C(OC(=O)c2cccc([N+](=O)[O-])c2)(C(=O)NC(C)(C)C)c2ccccc21]

$R_f$ (EtOAc/DCM=5/95): 0.58; ¹H NMR (400 MHz, CDCl₃): δ 8.82 (s, 1H), 8.46-8.44 (m, 1H), 8.30 (d, J=7.8 Hz, 1H), 7.68 (t, J=7.9 Hz, 1H), 7.41 (t, J=7.4 Hz, 2H), 7.10 (t, J=7.5 Hz, 1H), 6.95 (d, J=7.6 Hz, 1H), 6.78 (bs, 1H), 3.33 (s, 3H), 1.44 (s, 9H). ¹³C NMR (100 MHz, CDCl₃): δ 171.30, 162.49, 161.90, 148.40, 145.19, 135.59, 131.19, 130.38, 130.17, 128.34, 124.95, 124.80, 124.38, 123.58, 109.10, 81.61, 52.47, 28.67, 27.12. HRMS calculated [M+Na]⁺ for $C_{21}H_{21}O_6N_3Na$: 434.1323, found: 434.1323. FTIR (cm⁻¹): 3446, 3020, 2928, 2856, 1735, 1692, 1617, 1537, 1352, 1216, 1123, 757, 669.

Example 6

3-(tert-Butylcarbamoyl)-1-methyl-2-oxoindolin-3-yl 4-nitro benzoate (4f)

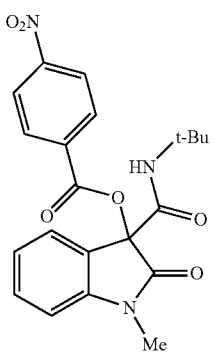 [SMILES: CN1C(=O)C(OC(=O)c2ccc([N+](=O)[O-])cc2)(C(=O)NC(C)(C)C)c2ccccc21]

$R_f$ (EtOAc/DCM=5/95): 0.63; ¹H NMR (400 MHz, CDCl₃): δ 8.31, (d, J=9.0 Hz, 2H), 8.16 (d, J=8.8 Hz, 2H), 7.43-7.39 (m, 2H), 7.10 (t, J=7.6 Hz, 1H), 6.95 (d, J=7.5 Hz, 1H), 6.73 (bs, 1H), 3.32 (s, 3H), 1.42 (s, 9H). ¹³C NMR (100 MHz, CDCl₃): δ 171.32, 162.34, 162.22, 151.06, 145.10, 133.96, 131.18, 131.16, 124.96, 124.12, 123.91, 123.58, 109.08, 81.54, 52.42, 28.65, 27.11. HRMS calculated [M+Na]⁺ for $C_{21}H_{21}O_6N_3Na$: 434.1323, found: 434.1322. FTIR (cm⁻¹): 3020, 2400, 1732, 1693, 1616, 1532, 1472, 1350, 1272, 1216, 758, 669.

Example 7

3-(tert-Butylcarbamoyl)-1-methyl-2-oxoindolin-3-yl 4-methoxy benzoate (4g)

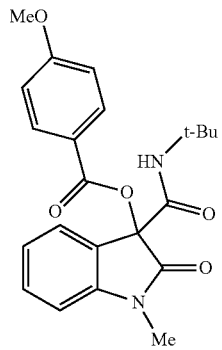 [SMILES: COc1ccc(C(=O)OC2(C(=O)NC(C)(C)C)C(=O)N(C)c3ccccc32)cc1]

$R_f$ (EtOAc/DCM=5/95): 0.59; ¹H NMR (400 MHz, CDCl₃); δ 7.92 (d, J=8.6 Hz, 2H), 7.38-7.32 (m, 2H), 7.05 (t, J=7.3 Hz, 1H), 6.94-6.89 (m, 3H), 6.79 (s, 1H), 3.86 (s, 3H), 3.31 (s, 3H), 1.43 (s, 9H). ¹³C NMR (100 MHz, CDCl₃); δ 171.91, 164.21, 163.44, 145.24, 132.34, 132.13, 130.70, 124.09, 120.85, 114.07, 113.76, 108.85, 81.07, 55.64, 52.17, 28.70, 27.01. HRMS calculated [M+H]⁺ for $C_{21}H_{25}O_5N_2$: 397.1758, found: 397.1757. FTIR (cm⁻¹); 3439, 3060, 2968, 1727, 1689, 1606, 1512, 1471, 1260, 1090, 732.

Example 8

3-(tert-Butylcarbamoyl)-1-methyl-2-oxoindolin-3-yl furan-2-carboxylate (4h)

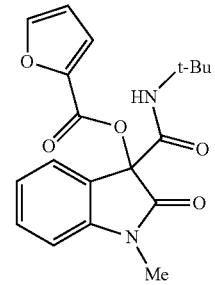 [SMILES: CN1C(=O)C(OC(=O)c2ccco2)(C(=O)NC(C)(C)C)c2ccccc21]

$R_f$ (EtOAc/DCM=5/95): 0.44; ¹H NMR (400 MHz, CDCl₃): δ 7.64 (s, 1H), 7.42-7.38 (m, 3H), 7.09 (t, J=7.4 Hz, 1H), 6.93 (d, J=7.98 Hz, 1H), 6.88 (bs, 1H), 6.57-6.56 (m, 1H), 3.32 (s, 3H), 1.46 (s, 9H). ¹³C NMR (100 MHz, CDCl₃): δ 171.23, 163.31, 155.51, 147.25, 145.47, 143.18, 130.93, 125.18, 123.69, 123.27, 120.13, 112.49, 108.98, 81.10, 52.20, 28.65, 27.01. HRMS calculated [M+H]⁺ for $C_{19}H_{21}O_5N_2$: 357.1445, found: 357.1444. FTIR (cm⁻¹): 33429, 3020, 2928, 1731, 1690, 1615, 1519, 1471, 1302, 1216, 112, 927, 757, 668.

Example 9

3-(tert-Butylcarbamoyl)-1-methyl-2-oxoindolin-3-yl thiophene-2-carboxylate (4i)

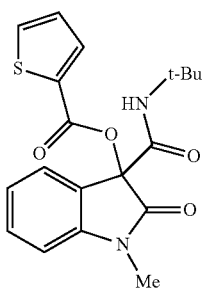 [SMILES: CN1C(=O)C(OC(=O)c2cccs2)(C(=O)NC(C)(C)C)c2ccccc21]

$R_f$ (EtOAc/DCM=5/95): 0.52; $^1$H NMR (400 MHz, CDCl$_3$): δ 7.79 (d, J=3.8 Hz, 1H), 7.63 (d, J=4.9 Hz, 1H), 7.37 (t, J=7.7 Hz, 1H), 7.33 (d, J=7.5 Hz, 1H), 7.12 (t, J=3.8 Hz, 1H), 7.06 (t, J=7.3 Hz, 1H), 6.90 (d, J=7.5 Hz, 1H), 6.78 (bs, 1H), 3.3 (s, 3H), 1.44 (s, 9H). $^{13}$C NMR (100 MHz, CDCl$_3$): δ 171.34, 163.21, 158.88, 145.38, 135.05, 133.77, 131.49, 130.92, 128.36, 125.15, 123.87, 123.28, 108.95, 81.34, 52.23, 28.68, 27.02. HRMS calculated [M+H]$^+$ for C$_{19}$H$_{21}$O$_4$N$_2$S: 373.1217, found: 373.1216. FTIR (cm$^{-1}$): 3438, 3020, 2400, 1729, 1690, 1617, 1494, 1472, 1361, 1215, 1072, 929, 759, 669.

Example 10

3-(tert-Butylcarbamoyl)-1-methyl-2-oxoindolin-3-yl benzofuran-2-carboxylate (4j)

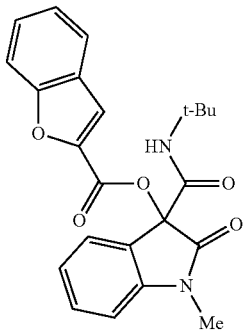 [SMILES: CN1C(=O)C(OC(=O)c2cc3ccccc3o2)(C(=O)NC(C)(C)C)c2ccccc21]

$R_f$ (EtOAc/DCM=5/95): 0.44; $^1$H NMR (400 MHz, CDCl$_3$); δ 7.71 (d, J=7.8 Hz, 1H), 7.60-7.58 (m, 2H), 7.53-7.49 (m, 1H), 7.43-7.33 (m, 3H), 7.07 (t, J=7.6 Hz, 1H), 6.94 (bs, 1H), 6.91 (d, J=8.1 Hz, 1H), 3.32 (s, 3H), 1.47 (s, 9H). $^{13}$C NMR (100 MHz, CDCl$_3$): δ 171.12, 163.18, 156.24, 156.02, 145.53, 143.88, 131.07, 128.54, 126.79, 124.94, 124.26, 123.96, 123.40, 123.22, 115.99, 112.44, 109.06, 81.40, 52.34, 28.69, 27.08. HRMS calculated [M+H]$^+$ for C$_{23}$H$_{23}$O$_5$N$_2$: 407.1601, found: 407.1599. FTIR (cm$^{-1}$) 3428, 2930, 1732, 1688, 1614, 1569, 1519, 1494, 1471, 1369, 1350, 1298, 1215, 1173, 1092, 1006, 748.

Example 11

3-(tert-Butylcarbamoyl)-1-methyl-2-oxoindolin-3-yl 1H-indole-2-carboxylate (4k)

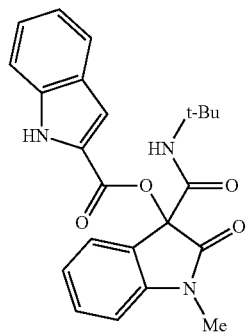 [SMILES: CN1C(=O)C(OC(=O)c2cc3ccccc3[nH]2)(C(=O)NC(C)(C)C)c2ccccc21]

$R_f$ (EtOAc/DCM=10/90): 0.55; $^1$H NMR (400 MHz, CDCl$_3$) δ 9.10 (bs, 1H), 7.67 (d, J=7.4 Hz, 1H), 7.34-7.19 (m, 5H), 7.13 (t, J=6.4 Hz, 1H), 7.02 (t, J=7.8 Hz, 1H), 6.85 (d, J=7.9 Hz, 1H), 6.79 (bs, 1H), 3.24 (s, 3H), 1.42 (s, 9H). $^{13}$C NMR (100 MHz, CDCl$_3$) δ 17.55, 163.21, 159.14, 145.24, 137.63, 130.88, 127.18, 126.23, 125.27, 125.12, 124.18, 123.35, 122.76, 121.30, 112.34, 109.98, 108.95, 81.28, 52.31, 28.69, 27.02. HRMS calculated [M+H]$^+$ for C$_{23}$H$_{24}$O$_4$N$_3$: 406.1761, found: 406.1762. FTIR (cm$^{-1}$): 3347, 3019, 2974, 2400, 1725, 1690, 1617, 1369, 1311, 1215, 758, 669.

Example 12

3-(tert-Butylcarbamoyl)-1-methyl-2-oxoindolin-3-yl picolinate (4l)

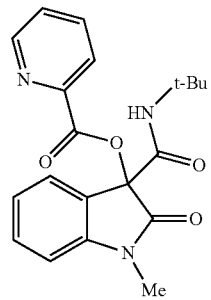

$R_f$ (EtOAc/DCM=20/80): 0.50; $^1$H NMR (400 MHz, CDCl$_3$): δ 8.76, (d, J=4.4 Hz, 1H), 8.02 (d, J=7.7 Hz, 1H), 7.82 (t, J=7.7 Hz, 1H), 7.53-7.50 (m, 1H), 7.35 (t, J=7.67 Hz, 1H), 7.31 (d, J=7.3 Hz, 1H), 7.25 (bs, 1H), 7.03 (t, J=7.5 Hz, 1H), 6.91 (d, J=7.9 Hz, 1H), 3.29 (s, 3H), 1.43 (s, 9H). $^{13}$C NMR (100 MHz, CDCl$_3$) δ 171.05, 163.74, 162.04, 150.00, 146.67, 145.66, 137.11, 130.86, 127.70, 125.60, 125.30, 123.34, 123.17, 108.87, 81.36, 52.06, 28.60, 26.94. HRMS calculated [M+H]$^+$ for C$_{20}$H$_{22}$O$_4$N$_3$: 368.1605, found: 368.1602. FTIR (cm$^{-1}$): 3407, 2969, 1734, 1686, 1614, 1590, 1433, 1115, 1025, 874, 748.

Example 13

3-(tert-Butylcarbamoyl)-1-methyl-2-oxoindolin-3-yl cinnamate (4m)

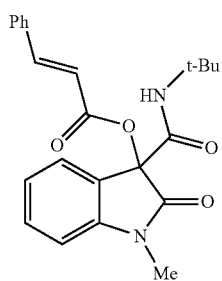 [SMILES: CN1C(=O)C(OC(=O)/C=C/c2ccccc2)(C(=O)NC(C)(C)C)c2ccccc21]

$R_f$ (EtOAc/DCM=5/95): 0.50; $^1$H NMR (400 MHz, CDCl$_3$): δ 7.67 (d, J=16.1 Hz, 1H), 7.50 (d, J=7.7 Hz, 2H), 7.41-7.35 (m, 4H), 7.33 (d, J=7.4 Hz, 1H), 7.09-7.06 (m, 1H), 6.90 (d, J=7.9 Hz, 1H), 6.74 (bs, 1H), 6.52 (d, J=16.26 Hz, 1H), 3.30 (s, 3H), 1.42 (s, 9H). $^{13}$C NMR (100 MHz, CDCl$_3$): δ 171.78, 164.08, 163.40, 147.82, 145.35, 133.91, 131.10, 130.72, 129.12, 129.05, 128.47, 128.40, 125.50, 123.83, 123.25, 115.83, 108.87, 81.13, 52.22, 28.69, 27.0 HRMS calculated [M+H]$^+$ for C$_{23}$H$_{25}$O$_4$N$_2$: 393.1809, found: 393.1807. FTIR (cm$^{-1}$): 3020, 2400, 1731, 1688, 1635, 1616, 1418, 1216, 1154, 1042, 929, 767, 669.

Example 14

3-(tert-Butylcarbamoyl)-1-methyl-2-oxoindolin-3-yl acetate (4n)

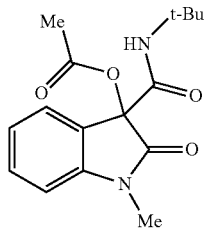 [SMILES: CC(=O)OC1(C(=O)NC(C)(C)C)C(=O)N(C)c2ccccc21]

$R_f$ (EtOAc/DCM=5/95): 0.45; $^1$H NMR (400 MHz, CDCl$_3$): δ 7.36 (t, J=8.2 Hz, 1H), 7.28-7.26 (m, 1H), 7.07 (t, J=7.6 Hz, 1H), 6.87 (d, J=7.01 Hz, 1H), 6.63 (bs, 1H), 3.26 (s, 3H), 2.17 (s, 3H), 1.39 (s, 9H). $^{13}$C NMR (100 MHz, CDCl$_3$): δ 171.67, 167.75, 163.30, 145.33, 130.70, 125.47, 123.50, 123.18, 108.90, 81.06, 52.15, 28.64, 26.93, 20.91. HRMS calculated [M+H]$^+$ for C$_{16}$H$_{21}$O$_4$N$_2$: 305.1496, found: 305.1494. FTIR (cm$^{-1}$): 3341, 3019, 1720, 1612, 1374, 1216, 1111, 771, 669, 507, 474, 487, 479.

Example 15

3-(tert-Butylcarbamoyl)-1-methyl-2-oxoindolin-3-yl propionate (4o)

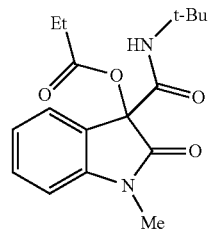 [SMILES: CCC(=O)OC1(C(=O)NC(C)(C)C)C(=O)N(C)c2ccccc21]

$R_f$ (EtOAc/DCM=5/95): 0.39; $^1$H NMR (400 MHz, CDCl$_3$): δ 7.35 (t, J=7.2 Hz, 1H), 7.26-7.23 (m, 1H), 7.05 (t, J=7.4 Hz, 1H), 6.87 (d, J=8.4. Hz, 1H), 6.62 (bs, 1H), 3.25 (s, 3H), 2.52-2.38 (m, 2H), 1.38 (s, 9H), 1.09 (t, J=7.5 Hz, 3H). $^{13}$C NMR (100 MHz, CDCl$_3$): δ 171.71, 171.29, 163.40, 145.32, 130.68, 125.54, 123.35, 123.16, 108.88, 80.89, 52.10, 28.63, 27.33, 26.92, 8.72. HRMS calculated [M+H]$^+$ for C$_{17}$H$_{23}$O$_4$N$_2$: 319.1652, found: 319.1651. FTIR (cm$^{-1}$): 3347, 2938, 1759, 1724, 1671, 1611, 1532, 1216, 1156, 1110, 890, 755.

Example 16

3-(tert-Butylcarbamoyl)-1-methyl-2-oxoindolin-3-yl 2-(4-methoxyphenyl)acetate (4p)

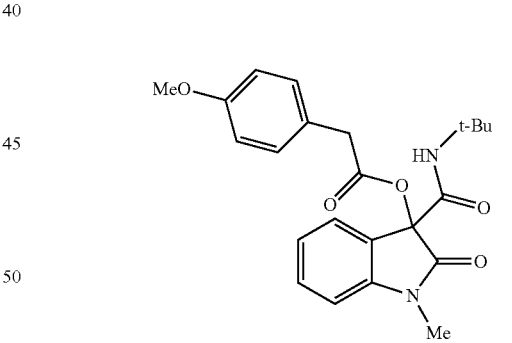

$R_f$ (EtOAc/DCM=5/95): 0.52; $^1$H NMR (400 MHz, CDCl$_3$): δ 7.33 (t, J=7.5 Hz, 1H), 7.18 (d, J=8.7 Hz, 2H), 7.10 (d, J=7.9 Hz, 1H), 7.02 (t, J=7.3 Hz, 1H), 6.89 (d, J=8.4 Hz, 2H), 6.84 (d, J=7.8 Hz, 1H), 6.32 (bs, 1H), 3.79 (s, 3H), 3.66 (s, 2H), 3.23 (s, 3H), 1.29 (s, 9H). $^{13}$C NMR (100 MHz, CDCl$_3$): δ 171.33, 168.39, 163.42, 159.03, 145.40, 130.74, 130.43, 125.34, 125.12, 123.12, 123.09, 114.36, 108.92, 81.08, 55.38, 52.0, 40.19, 28.55, 26.91. HRMS calculated [M+H]$^+$ for C$_{23}$H$_{27}$O$_5$N$_2$: 411.1914, found: 411.1913. FTIR (cm$^{-1}$): 3413, 3019, 1736, 1687, 1614, 1514, 1370, 1217, 1133, 1037, 770, 669.

Example 17

1-Benzyl-3-(tert-Butylcarbamoyl)-2-oxoindolin-3-yl benzoate (4q)

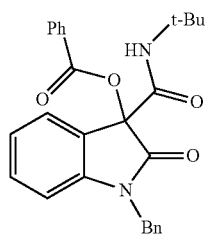 [SMILES: CC(C)(C)NC(=O)C1(OC(=O)c2ccccc2)C(=O)N(Cc2ccccc2)c2ccccc21]

$R_f$ (EtOAc/DCM=5/95): 0.61; $^1$H NMR (400 MHz, CDCl$_3$): δ 8.05 (d, J=7.2 Hz, 1H), 7.65 (t, J=7.2 Hz, 1H), 7.52 (t, J=8.0 Hz, 2H), 7.47 (d, J=8.0 Hz, 2H), 7.41-7.36 (m, 3H), 7.28 (t, J=7.6 Hz, 1H), 7.22 (t, J=7.6 Hz, 1H), 7.02 (t, J=7.3 Hz, 1H), 6.83 (bs, 1H), 6.72 (d, J=7.9 Hz, 1H), 5.08 (d, J=16.5 Hz, 2H), 5.07 (d, J=19.5 Hz, 1H), 1.49 (s, 9H). $^{13}$C NMR (100 MHz, CDCl$_3$) δ 171.80, 163.62, 163.34, 144.28, 135.29, 134.05, 130.63, 130.04, 128.95, 128.81, 128.66, 127.68, 127.20, 125.32, 123.87, 123.27, 110.09, 81.44, 52.25, 44.99, 28.75. HRMS calculated [M+H]+ for C$_{27}$H$_{27}$O$_4$N$_2$: 443.1965, found: 443.1961. FTIR (cm$^{-1}$) 3020, 2926, 2855, 1731, 1688, 1615, 1516, 1468, 1367, 1268, 1216, 1178, 1088, 770, 669.

Example 18

1-Allyl-3-(tert-Butylcarbamoyl)-2-oxoindolin-3-yl benzoate (4r)

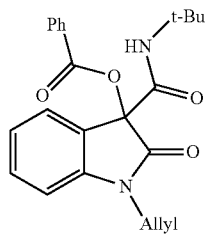

$R_f$ (EtOAc/DCM=5/95): 0.56; $^1$H NMR (400 MHz, CDCl$_3$): δ 7.99 (d, J=7.5 Hz, 2H), 7.61 (t, J=7.4 Hz, 1H), 7.47 (t, J=7.4 Hz, 2H), 7.35-7.31 (m, 2H), 7.05 (t, J=7.6 Hz, 1H), 6.89 (d, J=7.1 Hz, 1H), 6.78 (bs, 1H), 5.93-5.88 (m, 1H), 5.45 (d, J=19.2 Hz, 1H), 5.27 (d, J=10.5 Hz, 1H), 4.45-4.42 (m, 2H), 1.44 (s, 9H). $^{13}$C NMR (100 MHz, CDCl$_3$): δ 171.42, 163.56, 163.31, 144.40, 134.60, 130.78, 130.61, 129.97, 128.77, 128.61, 125.29, 123.88, 123.17, 117.97, 109.86, 81.29, 52.19, 42.95, 28.70. HRMS calculated [M+H]+ for C$_{23}$H$_{25}$O$_4$N$_2$: 393.1809, found: 393.1805. FTIR (cm$^{-1}$) 3439, 3020, 2400, 1734, 1689, 1615, 1517, 1424, 1267, 1215, 1115, 929, 850, 780, 669.

Example 19

3-(tert-Butylcarbamoyl)-2-oxoindolin-3-yl benzoate (4s)

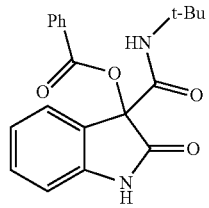 [SMILES: CC(C)(C)NC(=O)C1(OC(=O)c2ccccc2)C(=O)Nc2ccccc21]

$R_f$ (EtOAc/DCM=10/90): 0.30; $^1$H NMR (400 MHz, CDCl$_3$): δ 8.02-7.90 (m, 3H), 7.66-7.59 (m, 1H), 7.48 (t, J=7.6 Hz, 2H), 7.30 (t, J=7.7 Hz, 2H), 7.04 (t, J=7.3 Hz, 1H), 6.90 (d, J=7.7 Hz, 1H), 6.74 (s, 1H), 1.44 (s, 9H). $^{13}$C NMR (100 MHz, CDCl$_3$): δ 173.03, 163.83, 163.26, 142.48, 134.08, 130.78, 130.03, 128.82, 128.57, 125.54, 124.33, 123.14, 110.92, 81.50, 52.29, 30.93, 28.69. HRMS calculated [M+H]$^+$ for C$_{20}$H$_{21}$O$_4$N$_2$: 353.1496, found: 353.1495. FTIR (cm$^{-1}$): 3683, 3436, 3019, 2977, 2400, 1736, 1689, 1623, 1519, 1268, 1215, 1110, 929, 758, 669.

Example 20

3-(tert-Butylcarbamoyl)-1-methyl-5-nitro-2-oxoindolin-3-yl benzoate (4t)

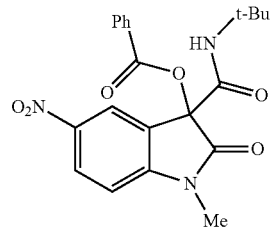 [SMILES: CN1C(=O)C(OC(=O)c2ccccc2)(C(=O)NC(C)(C)C)c2cc([N+](=O)[O-])ccc21]

$R_f$ (EtOAc/DCM=5/95): 0.55; $^1$H NMR (400 MHz, CDCl$_3$): δ 8.35 (d, J=8.5 Hz, 1H), 8.19 (m, 1H), 7.96 (d, J=6.8 Hz, 2H), 7.65 (t, J=8.5 Hz, 1H), 7.50 (t, J=6.8 Hz, 2H), 7.01 (d, J=8.5 Hz, 1H), 6.77 (bs, 1H), 3.38 (s, 3H), 1.45 (s, 9H). $^{13}$C NMR (100 MHz, CDCl$_3$): δ 171.82, 163.79, 162.22, 150.93, 143.84, 134.62, 130.06, 129.04, 127.76, 126.36, 119.79, 108.59, 80.19, 52.71, 28.69, 27.50. HRMS calculated [M+H]+ for C$_{21}$H$_{22}$O$_6$N$_3$: 412.1503, found: 412.1502. FTIR (cm$^{-1}$) 3684, 3437, 3020, 2400, 1736, 1691, 1617, 1524, 1496, 1337, 1215, 1267, 1108, 1067, 929, 768, 669, 625.

Example 21

3-(tert-Butylcarbamoyl)-5-fluoro-1-methyl-2-oxoindolin-3-yl benzoate (4u)

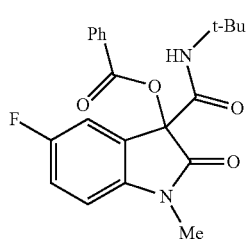 [SMILES: CN1C(=O)C(OC(=O)c2ccccc2)(C(=O)NC(C)(C)C)c2cc(F)ccc21]

R$_f$ (EtOAc/DCM=5/95): 0.44; $^1$H NMR (400 MHz, CDCl$_3$); δ 7.98-7.96 (m, 2H), 7.62 (t, J=7.5 Hz, 1H), 7.48 (t, J=7.9 Hz, 2H), 7.13-7.06 (m, 2H), 6.85-6.83 (dd, J$_1$=4.0 Hz, J$_2$=8.8 Hz, 1H), 6.80 (bs, 1H), 3.31 (s, 3H), 1.44 (s, 9H). $^{13}$C NMR (100 MHz, CDCl$_3$); δ 171.51, 163.78, 162.67, 159.44 (d, J=244.2 Hz), 141.20, 134.22, 130.0, 128.66, 128.31, 126.52, 126.43, 117.02 (d, J=24.4 Hz), 112.72 (d, J=25.6 Hz), 109.49 (d, J=7.8 Hz), 80.97, 52.37, 28.66, 27.19. HRMS calculated [M+H]$^+$ for C$_{21}$H$_{22}$O$_4$N$_2$F: 385.1558, found: 385.1556. FTIR (cm$^{-1}$) 3384, 2973, 2934, 1731, 1671, 1623, 1523, 1497, 1473, 1454, 1369, 1351, 1268, 1233, 1162, 1112, 1008, 820, 711, 559.

Example 22

3-(tert-Butylcarbamoyl)-5-chloro-1-methyl-2-oxoindolin-3-yl benzoate (4v)

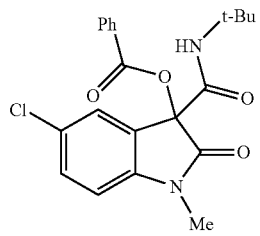 [SMILES: CN1C(=O)C(OC(=O)c2ccccc2)(C(=O)NC(C)(C)C)c2cc(Cl)ccc21]

R$_f$ (EtOAc/DCM=5/95): 0.69; $^1$H NMR (400 MHz, CDCl$_3$): δ 7.98 (d, J=7.9 Hz, 2H), 7.64-7.61 (m, 1H), 7.48 (t, J=2.9 Hz, 2H), 7.36-7.33 (m, 2H), 6.85 (d, J=8.4 Hz, 1H), 6.80 (bs, 1H), 3.30 (s, 3H), 1.44 (s, 9H). $^{13}$C NMR (100 MHz, CDCl$_3$): δ 171.36, 163.74, 162.66, 143.85, 134.26, 130.69, 130.21, 130.01, 128.89, 128.69, 128.52, 128.26, 126.68, 124.75, 109.86, 80.80, 52.41, 28.68, 27.18. HRMS calculated [M+H]$^+$ for C$_{21}$H$_{22}$O$_4$N$_2$Cl: 401.1263, found: 401.1263. FTIR (cm$^{-1}$): 3439, 3020, 1732, 1692, 1615, 1492, 1366, 1268, 1216, 1108, 759, 709, 669.

Example 23

5-Bromo-3-(tert-Butylcarbamoyl)-1-methyl-2-oxoindolin-3-yl benzoate (4w)

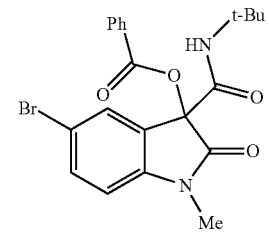

R$_f$ (EtOAc/DCM=5/95): 0.45; $^1$H NMR (400 MHz, CDCl$_3$): δ 7.97 (d, J=6.8 Hz, 2H), 7.63 (t, J=6.6 Hz, 1H), 7.51-7.46 (m, 4H), 6.79 (d, J=8.3 Hz, 2H), 3.29 (s, 3H) 1.44 (s, 9H). $^{13}$C NMR (100 MHz, CDCl$_3$): δ 171.27, 163.73, 162.66, 144.36, 130.02, 128.89, 128.54, 128.26, 127.42, 127.02, 115.92, 110.34, 80.73, 52.42, 28.69, 27.16. HRMS: calculated [M+H]$^+$ for C$_{21}$H$_{22}$O$_4$N$_2$Br: 447.0737, found: 447.0727. FTIR (cm$^{-1}$) 3439, 3020, 2972, 2400, 1732, 1691, 1611, 1453, 1107, 757.

Example 24

3-(Cyclohexylcarbamoyl)-1-methyl-2-oxoindolin-3-yl benzoate (4x)

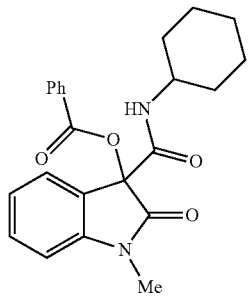 [SMILES: CN1C(=O)C(OC(=O)c2ccccc2)(C(=O)NC2CCCCC2)c2ccccc21]

R$_f$ (EtOAc/DCM=5/95): 0.50; $^1$H NMR (400 MHz, CDCl$_3$): δ 7.99 (d, J=7.4 Hz, 2H), 7.60 (t, J=7.5 Hz, 1H), 7.46 (t, J=7.8 Hz, 2H), 7.39-7.34 (m, 2H), 7.06 (t, J=7.7 Hz, 1H), 6.90 (d, J=8.04 Hz, 1H), 6.80 (bs, 1H), 3.88-3.80 (m, 1H), 3.32 (s, 3H), 2.04-1.95 (m, 2H), 1.74-1.71 (m, 2H), 1.64-1.60 (m, 1H), 1.43-1.21 (m, 5H). $^{13}$C NMR (100 MHz, CDCl$_3$): δ 171.55, 163.79, 163.32, 145.19, 134.02, 130.85, 129.99, 128.77, 128.57, 125.04, 124.26, 123.27, 108.92, 81.01, 49.0, 32.88, 32.64, 27.03, 25.55, 24.77, 24.72. HRMS calculated [M+H]+ for C$_{23}$H$_{25}$O$_4$N$_2$: 393.1809, found: 393.1799. FTIR (cm$^{-1}$): 3020, 2936, 2858, 1732, 1683, 1617, 1518, 1375, 1270, 1215, 929, 759, 669.

Example 25

3-(Isopropylcarbamoyl)-1-methyl-2-oxoindolin-3-yl benzoate (4y)

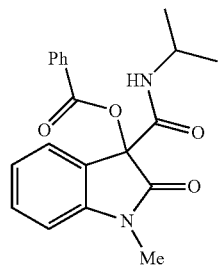 [SMILES: CC(C)NC(=O)C1(OC(=O)c2ccccc2)C(=O)N(C)c2ccccc21]

R$_f$ (EtOAc/DCM=5/95): 0.36; $^1$H NMR (400 MHz, CDCl$_3$): δ 7.99 (d, J=7.19 Hz 2H), 7.61 (t, J=7.6 Hz 1H), 7.46 (t, J=7.8 Hz 2H), 7.39-7.35 (m, 2H), 7.07 (t, J=7.4 Hz, 1H), 6.92 (d, J=7.7 Hz, 1H), 6.74 (d, J=7.06 Hz, 1H), 4.17-4.10 (m, 1H), 3.32 (s, 3H), 1.29 (d, J=6.7 Hz, 3H), 1.25 (d, J=6.7 Hz, 3H). $^{13}$C NMR (100 MHz, CDCl$_3$): δ 171.55, 163.81, 163.38, 145.21, 134.03, 130.85, 130, 128.77, 128.59, 125.02, 124.29, 123.29, 108.92, 80.99, 42.41, 27.03, 22.69, 22.48. HRMS calculated [M+H]$^+$ for C$_{20}$H$_{21}$O$_4$N$_2$: 353.1496, found: 353.1495. FTIR (cm$^{-1}$): 3020, 2406, 1732, 1679, 1616, 1416, 1270, 1215, 1021, 758, 669.

Example 26

3-((2-Ethoxy-2-oxoethyl)carbamoyl)-1-methyl-2-oxoindolin-3-yl benzoate (4z)

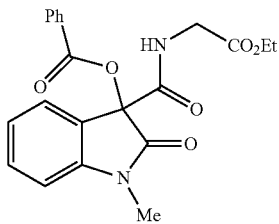 [SMILES: CCOC(=O)CNC(=O)C1(OC(=O)c2ccccc2)C(=O)N(C)c2ccccc21]

R$_f$ (EtOAc/DCM=5/95): 0.37; $^1$H NMR (400 MHz, CDCl$_3$) δ 8.08-8.04 (m, 2H), 7.60-7.33 (m, 6H), 7.07 (t, J=7.7 Hz, 1H), 6.92 (d, J=7.7 Hz, 1H), 4.30-4.20 (m, 3H), 4.08-4.02 (dd, J$_1$=4.5 Hz, J$_2$=18.6 Hz, 1H), 3.32 (s, 3H), 1.31 (t, J=6.3 Hz, 3H). $^{13}$C NMR (100 MHz, CDCl$_3$) δ 171.02, 169.34, 164.84, 163.59, 145.37, 134.11, 133.67, 131.08, 130.22, 130.11, 128.81, 128.53, 128.35, 124.39, 123.87, 123.33, 109.07, 81.22, 61.96, 41.81, 27.07, 14.25. H.RMS calculated [M+H]$^+$ for C$_{21}$H$_{21}$O$_6$N$_2$: 397.1394, found: 397.1393. FTIR (cm$^{-1}$) 3430, 3020, 2400, 1732, 1693, 1616, 1524, 1473, 1422, 1273, 1215, 1108, 759, 669, 497.

Example 27

N-(tert-Butyl)-1-methyl-3-(2-nitrophenoxy)-2-oxoindoline-3-carboxamide (6a)

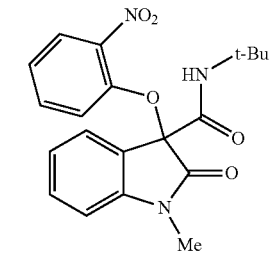 [SMILES: CN1C(=O)C(Oc2ccccc2[N+](=O)[O-])(C(=O)NC(C)(C)C)c2ccccc21]

R$_f$ (EtOAc/DCM=5/95): 0.45; $^1$H NMR (400 MHz, CDCl$_3$) δ 7.98 (d, J=7.5 Hz, 1H), 7.78 (s, 1H), 7.37 (t, J=7.6, 1H), 7.28-7.19 (m, 2H), 7.07-7.01 (m, 2H), 6.92 (d, J=8.8 Hz, 1H), 6.46 (d, J=6.8 Hz, 1H), 3.32 (s, 3H), 1.45 (s, 9H). $^{13}$C NMR (100 MHz, CDCl$_3$) δ 171.19, 164.54, 148.59, 145.00, 140.76, 135.00, 131.57, 126.81, 123.92, 123.90, 123.25, 118.43, 109.47, 85.19, 52.21, 28.65, 27.02. H.RMS calculated [M+H]$^+$ for C$_{20}$H$_{22}$O$_5$N$_3$: 384.1554, found: 384.1554. FTIR (cm$^{-1}$) 3389, 3063, 2971, 2252, 1735, 1685, 1609, 1348, 911, 733.

Example 28

5-Bromo-N-(tert-butyl)-1-methyl-3-(2-nitrophenoxy)-2-oxoindoline-3-carboxamide (6b)

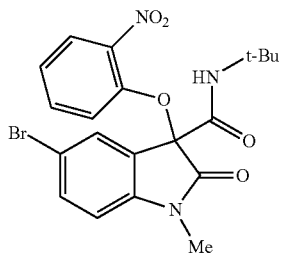 [SMILES: CN1C(=O)C(Oc2ccccc2[N+](=O)[O-])(C(=O)NC(C)(C)C)c2cc(Br)ccc21]

R$_f$ (EtOAc/DCM=5/95): 0.45; $^1$H NMR (200 MHz, CDCl$_3$): δ 8.05-8.01 (m, 1H), 7.77 (s, 1H), 7.55-7.50 (m, 1H), 7.35-7.26 (m, 2H), 7.10 (t, J=7.2 Hz, 1H), 6.82 (d, J=8.3 Hz, 1H), 6.39 (d, J=8.3 Hz, 1H), 3.29 (s, 3H) 1.45 (s, 9H). $^{13}$C NMR (100 MHz, CDCl$_3$): δ 170.41, 163.88, 148.35, 143.98, 140.61, 135.14, 134.45, 127.10, 126.63, 123.50, 117.87, 116.60, 110.92, 84.69, 52.43, 50.35, 28.64, 27.16. HRMS calculated [M+H]$^+$ for C$_{20}$H$_{21}$O$_5$N$_3$: 462.0659, found: 462.0662. FTIR (cm$^{-1}$) 3390, 3020, 2400, 1740, 1688, 1607, 1526, 1347, 1215, 1104, 1037, 858, 757, 669.

Example 29

N-Cyclohexyl-1-methyl-3-(2-nitrophenoxy)-2-oxoindoline-3-carboxamide (6c)

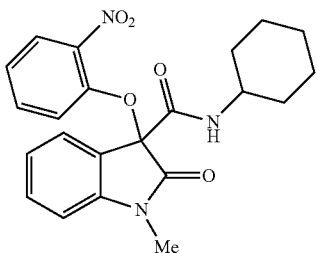 [SMILES: CN1C(=O)C(Oc2ccccc2[N+](=O)[O-])(C(=O)NC2CCCCC2)c2ccccc21]

$R_f$ (EtOAc/DCM 5/99): 0.30; $^1$H NMR (400 MHz, CDCl$_3$): $^1$H NMR (400 MHz, CDCl$_3$):δ 7.98 (d, J=7.12 Hz, 1H), 7.78 (s, 1H), 7.37-7.19 (m, 3H), 7.05-6.91 (m, 3H), 6.87 (d, J=7.42 Hz, 1H), 3.78 (s, 1H), 3.31 (s, 3H), 1.99 (s, 2H), 1.78 (s, 2H), 1.60 (s, 1H), 1.39-1.38 (m, 5H) $^{13}$C NMR (100 MHz, CDCl$_3$): δ 171.03, 164.52, 148.62, 144.97, 140.84, 134.99, 131.59, 126.81, 124.41, 124.08, 123.86, 123.29, 118.57, 109.46, 85.11, 48.94, 32.79, 32.64, 27.04, 25.59, 24.75. HRMS calculated [M+H]$^+$ for C$_{22}$H$_{24}$O$_5$N$_3$: 410.1710, found: 410.1711. FTIR (cm$^{-1}$) 3944, 3054, 2987, 2685, 2410, 2305, 1731, 1604, 1421, 1265, 1021, 896, 739, 706.

Example 30

5-Bromo-N-(tert-Butyl)-3-hydroxy-1-methyl-2-oxoindoline-3-carboxamide (7)

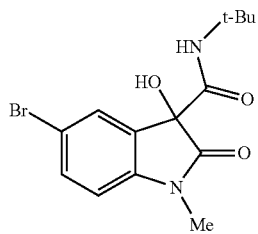 [SMILES: CN1C(=O)C(O)(C(=O)NC(C)(C)C)c2cc(Br)ccc21]

$R_f$ (EtOAc/DCM=20/80): 0.41; $^1$H NMR (400 MHz, CDCl$_3$): δ 7.46 (d, J=6.4 Hz, 1H), 7.36 (d, J=1.8 Hz, 1H), 6.72 (d, J=8.9 Hz, 1H), 6.64 (bs, 1H), 4.99 (s, 1H), 3.14 (s, 3H), 1.33 (s, 9H). $^{13}$C NMR (100 MHz, CDCl$_3$): δ 174.70, 166.99, 143.76, 133.34, 130.69, 126.84, 116.21, 110.53, 78.37, 52.05, 28.67, 26.85. HRMS calculated [M+H]$^+$ for C$_{14}$H$_{18}$O$_3$N$_2$Br: 341.0495, found: 341.0497. FTIR (cm$^{-1}$): 3373, 2969, 2923, 1734, 1607, 1488, 1366, 1218, 1099, 878, 824, 760.

Example 10

Antitubercular Activity

The compounds were tested for their Anti Mycobacterial ability on *M. smegmatis* MC$^2$ 155 strain. The series of compounds were obtained in 10 mM stock concentrations. Further, each compound was diluted with the required 100% (v/v) DMSO to achieve a working concentration of 1.5 mM. The inoculum for the assay was prepared by reviving a glycerol stock in Middlebrook 7H9 broth supplemented with 0.1% Tween 80 and 0.5% Glycerol. At the time of inoculation, 10% ADS was added to the media and the culture was incubated in a shaker incubator at 37° C. and 200 rpm. The O.D. of the inoculum reached to 0.8-1 approximately, a secondary inoculum was inoculated and subsequently incubated. This was incubated overnight till the O.D. of the inoculum reached 0.4 approx., following which the inoculum was diluted 1:1000 times. In a 96 well microtiter plate, a 2 μL aliquot of the 1.5 mM dilution of compound was added to each well in triplicate, to which 98 μL of inoculum dilution was added, making the final concentration of compound 30 μM. To each plate a set of controls was added to better ascertain the activity of the compounds. These included DMSO, which was taken as a growth control, and media control (Blank) and Rifampicin and Isoniazid, which were taken as positive controls of inhibition of *Mycobacterium smegmatis*. After the completion of the period of 32 hrs, the absorbance of the inoculum in wells was measured at 600 nm using a Multi Mode Reader. Absorbance is considered directly proportional to the increase in growth of bacteria, thus it gives a measure of the growth of bacteria in each well. Percentage inhibition was determined against DMSO. The percentage inhibition values of the compounds tested are given in the Table 5.

TABLE 5

Percentage inhibition values of compounds

TABLE 5-continued

Percentage inhibition values of compounds

R = H, (18.623)
R = F, (24.550)
R = Cl, (42.717)
R = Br, (17.349)

(−5.237)

R = NO$_2$, (21.522)
R = OMe, (43.505)

R$^1$ = Bn, (42.881)
R$^1$ = allyl, (35.352)
R$^1$ = H, (19.067)

TABLE 5-continued

Percentage inhibition values of compounds

R$^2$ = NO$_2$, (NA)
R$^2$ = F, (5.237)
R$^2$ = Cl, (9.493)
R$^2$ = Br, (23.352)

X = O, (24.059)
X = S, (30.769)

(26.350)

(9.002)

TABLE 5-continued

Percentage inhibition values of compounds (5.237)

(14.730)

(7.038)

$R^3$ = Me, (19.640)
$R^3$ = Et, (−1.637)

(44.190)

TABLE 5-continued

Percentage inhibition values of compounds (−5.237)

(−8.020)

% inhibition in parentheses

ADVANTAGES OF THE INVENTION a. One step, one pot synthesis
b. Solvent-free process carried out in the presence of air
c. Efficient method for the synthesis of variety of oxindoles
d. Process of synthesis is tunable
e. Products were formed in high yield
f. The products are anticipated to show excellent biological activities

We claim:
1. An oxindole compound of formula A,

Formula A wherein, $R^1$=methyl, H, Allyl, Benzyl, or Phenyl;
$R^2$=H, Br, Cl, F, or $NO_2$;
$R^3$=methyl, ethyl, t-butyl, substituted alkenyl or substituted or un-substituted aryl;
$R^4$=t-Bu, i-Pr, or $CH_2$—$CO_2Et$; and $R^5 = $ 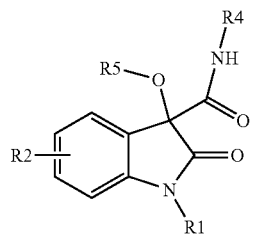 , or H.

2. The oxindole compound of formula A of claim 1, wherein formula A is selected from the group consisting of:

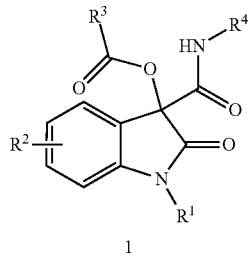

Formula 4 wherein, $R^1$=methyl, H, Allyl, benzyl or Phenyl;
$R^2$=H, Br, Cl, F, or $NO_2$;
$R^3$=methyl, ethyl, t-butyl, substituted alkenyl or substituted or un-substituted aryl; and
$R^4$=t-Bu, i-Pr, or $CH_2$—$CO_2Et$ and,

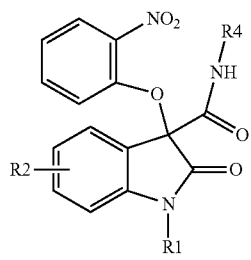

Formula 6 wherein, $R^1$=methyl, H, Allyl, Benzyl or Phenyl;
$R^2$=H, Br, Cl, F, or $NO_2$;
$R^3$=substituted or un-substituted aryl, or substituted alkenyl or methyl, ethyl or t-butyl; and
$R^4$=t-Bu, i-Pr, or $CH_2$—$CO_2Et$.

3. An oxindole compound selected from the group consisting of
3-(tert-Butylcarbamoyl)-1-methyl-2-oxoindolin-3-yl benzoate,
3-(tert-Butylcarbamoyl)-1-methyl-2-oxoindolin-3-yl 2-fluoro benzoate,
3-(tert-Butylcarbamoyl)-1-methyl-2-oxoindolin-3-yl 2-chloro benzoate,
3-(tert-Butylcarbamoyl)-1-methyl-2-oxoindolin-3-yl 2-bromo benzoate,
3-(tert-Butylcarbamoyl)-1-methyl-2-oxoindolin-3-yl 3-nitro benzoate,
3-(tert-Butylcarbamoyl)-1-methyl-2-oxoindolin-3-yl 4-nitro benzoate,
3-(tert-Butylcarbamoyl)-1-methyl-2-oxoindolin-3-yl 4-methoxybenzoate,
3-(tert-Butylcarbamoyl)-1-methyl-2-oxoindolin-3-yl furan-2-carboxylate,
3-(tert-Butylcarbamoyl)-1-methyl-2-oxoindolin-3-ylthiophene-2-carboxylate,
3-(tert-Butylcarbamoyl)-1-methyl-2-oxoindolin-3-yl benzofuran-2-carboxylate,
3-(tert-Butylcarbamoyl)-1-methyl-2-oxoindolin-3-yl 1H-indole-2-carboxylate,
3-(tert-Butylcarbamoyl)-1-methyl-2-oxoindolin-3-yl picolinate,
3-(tert-Butylcarbamoyl)-1-methyl-2-oxoindolin-3-yl cinnamate,
3-(tert-Butylcarbamoyl)-1-methyl-2-oxoindolin-3-yl acetate,
3-(tert-Butylcarbamoyl)-1-methyl-2-oxoindolin-3-yl propionate,
3-(tert-Butylcarbamoyl)-1-methyl-2-oxoindolin-3-yl 2-(4-methoxyphenyl)acetate,
1-Benzyl-3-(tert-Butylcarbamoyl)-2-oxoindolin-3-yl benzoate,
1-Allyl-3-(tert-Butylcarbamoyl)-2-oxoindolin-3-yl benzoate,
3-(tert-Butylcarbamoyl)-2-oxoindolin-3-yl benzoate,
3-(tert-Butylcarbamoyl)-1-methyl-5-nitro-2-oxoindolin-3-yl benzoate,
3-(tert-Butylcarbamoyl)-5-fluoro-1-methyl-2-oxoindolin-3-yl benzoate,
3-(tert-Butylcarbamoyl)-5-chloro-1-methyl-2-oxoindolin-3-yl benzoate,
5-Bromo-3-(tert-Butylcarbamoyl)-1-methyl-2-oxoindolin-3-yl benzoate,
3-(Isopropylcarbamoyl)-1-methyl-2-oxoindolin-3-yl benzoate,
3-((2-Ethoxy-2-oxoethyl)carbamoyl)-1-methyl-2-oxoindolin-3-yl benzoate,
N-(tert-Butyl)-1-methyl-3-(2-nitrophenoxy)-2-oxoindoline-3-carboxamide,
5-Bromo-N-(tert-butyl)-1-methyl-3-(2-nitrophenoxy)-2-oxoindoline-3carboxamide, and
5-Bromo-N-(tert-Butyl)-3-hydroxy-1-methyl-2-oxoindoline-3-carboxamide.

4. A process for the synthesis of oxindole compound of general formula A of claim 1, comprising the steps of:
(a) reacting carboxylic acid 2 $R^3$—$CO_2H$ or electron-deficient phenol 5

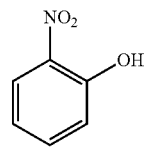

5 with an isatin derivative 1

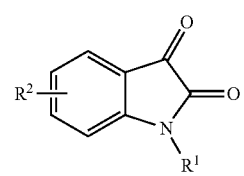

1 and an isocyanide 3 CN—$R^4$ in the presence of air to obtain a reaction mixture; wherein $R^1$=methyl, H, Allyl, benzyl or Phenyl, $R^2$=H, Br, Cl, F, or $NO_2$, $R^3$=methyl, ethyl, t-butyl, substituted alkenyl or substituted or un-substituted aryl and $R^4$=t-Bu, i-Pr, or $CH_2$—$CO_2Et$;

(b) heating the reaction mixture as obtained in step (a) under solvent-free conditions to obtain a crude reaction mixture; and (c) purifying the crude reaction mixture obtained in step (b) by column chromatography to obtain the oxindole compound of formula A consisting of formula 4

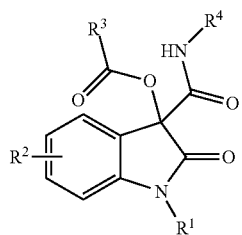

formula 4 and formula 6

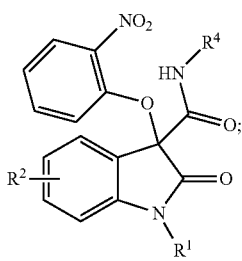

formula 6 or (d) hydrolyzing the crude reaction mixture obtained in step (b) to obtain the oxindole compound of formula A consisting of formula 7

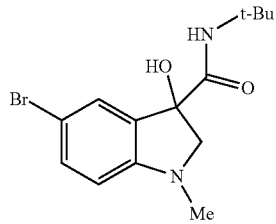

formula 7

5. The process of claim 4, wherein the heating in step (b) is carried out in a preheated oil bath at a temperature from 60 to 100° C. for a period of 8-12 h.

6. The process of claim 4, wherein the carboxylic acid is selected from the group consisting of heteroaryl carboxylic acids, N-unprotected indole 2-carboxylic acid, α, β-unsaturated substituted alkenyl acid, substituted or unsubstituted benzoic acid and aliphatic acids selected from acetic acid, propionic acid and pivalic acid.

7. The process of claim 6, wherein the carboxylic acid is acetic acid.

8. The process of claim 4, wherein the yield of oxindole compound of formula A under solvent-free conditions in the presence of air is in the range of 80% to 96%.

9. The process of claim 4, wherein the electron-deficient phenol of formula 5 is used for the synthesis of O-arylated oxindole derivative of formula 6.

10. The process of claim 4, wherein the yield of O-arylated oxindole derivatives 6 is 40% to 55%.

11. The oxindole compound of claim 1, wherein $R^3$ is an α, β-unsaturated substituted alkenyl group.

12. The oxindole compound of claim 1, wherein $R^3$ is

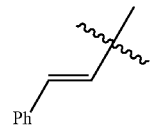

* * * * *